(12) United States Patent
Ueda et al.

(10) Patent No.: US 7,871,801 B2
(45) Date of Patent: Jan. 18, 2011

(54) L-AMINO ACID-PRODUCING BACTERIUM AND A METHOD FOR PRODUCING L-AMINO ACIDS

(75) Inventors: Takuji Ueda, Kawasaki (JP); Yuji Joe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 39 days.

(21) Appl. No.: 12/056,414

(22) Filed: Mar. 27, 2008

(65) Prior Publication Data

US 2009/0275091 A1  Nov. 5, 2009

Related U.S. Application Data

(63) Continuation of application No. PCT/JP2006/319635, filed on Sep. 25, 2006.

(60) Provisional application No. 60/723,937, filed on Oct. 6, 2005.

(30) Foreign Application Priority Data

Sep. 27, 2005 (JP) .............................. 2005-279026
Dec. 14, 2005 (JP) .............................. 2005-360672

(51) Int. Cl.
C12P 13/04    (2006.01)
C12N 9/00     (2006.01)
C12N 9/24     (2006.01)
C12N 1/20     (2006.01)
C12N 15/00    (2006.01)
C07H 21/04    (2006.01)

(52) U.S. Cl. ................. 435/106; 435/183; 435/200; 435/252.3; 435/320.1; 536/23.2

(58) Field of Classification Search ................. None
See application file for complete search history.

(56) References Cited

U.S. PATENT DOCUMENTS

| 7,306,933 B2 | 12/2007 | Van Dien et al. |
| 2006/0019355 A1 | 1/2006 | Ueda et al. |
| 2006/0088919 A1 | 4/2006 | Rybak et al. |
| 2006/0160191 A1 | 7/2006 | Kataoka et al. |

FOREIGN PATENT DOCUMENTS

WO    WO03004670    *   1/2003

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
U.S. Appl. No. 11/759,419, filed Jun. 7, 2007, Ueda et al.
U.S. Appl. No. 11/877,726, filed Oct. 24, 2007, Van Dien et al.
U.S. Appl. No. 12/056,390, filed Mar. 27, 2008, Ueda et al.

* cited by examiner

*Primary Examiner*—Christian L Fronda
(74) *Attorney, Agent, or Firm*—Shelly Guest Cermak; Cermak Nakajima LLP

(57) ABSTRACT

A method for producing an L-amino acid is provided which includes culturing in a medium a microorganism of the Enterobacteriaceae family which has an ability to produce an L-amino acid and which has been modified so as to enhance the mannose PTS activity, accumulating the L-amino acid in the medium or in cells, and collecting the L-amino acid from the medium or cells.

6 Claims, 3 Drawing Sheets

L-AMINO ACID-PRODUCING BACTERIUM AND A METHOD FOR PRODUCING L-AMINO ACIDS

This application claims priority under 35 U.S.C. §119 to Japanese Patent Application No. 2005-279026, filed on Sep. 27, 2005, U.S. Provisional Patent Application No. 60/723, 937, filed on Oct. 6, 2005, and Japanese Patent Application No. 2005-360672, filed on Dec. 14, 2005, and is a continuation application under 35 U.S.C. §120 to PCT Patent Application No. PCT/JP2006/319635, filed on Sep. 25, 2006, the contents of which are incorporated by reference in their entireties. The Sequence Listing filed electronically herewith is also hereby incorporated by reference in its entirety (File Name: US-253_Seq_List_Copy_1; File Size: 87 KB; Date Created: Mar. 27, 2008).

BACKGROUND OF THE INVENTION

1. Technical Field

The present invention relates to a method for producing an L-amino acid using a microorganism, and more specifically, to a method for producing an L-amino acid, such as L-lysine, L-threonine, and L-glutamic acid, etc. L-lysine and L-threonine are typically used as animal feed additives, health food ingredients, amino acid infusions, etc., and L-glutamic acid is typically used as a seasoning. Therefore, these are industrially useful L-amino acids.

2. Background Art

L-amino acids are industrially produced employing fermentation methods, using microorganisms of the genera *Brevibacterium*, *Corynebacterium*, and *Escherichia*, etc. (EP0857784, 0999267, 1170358, JP11-192088A, WO00/53726, WO96/17930, WO03/04674). Wild-type microorganisms, artificial mutants of said bacterial strains, and microorganisms which have been modified so that the activities of the L-amino acid biosynthesis enzymes are enhanced by recombinant DNA techniques are typically used for L-amino acid production.

Known methods for enhancing the ability of various strains to produce an L-amino acid include modifying the L-amino acid uptake or export. For example, to modify the uptake, the ability to produce L-amino acids is enhanced by deleting or reducing the L-amino acid uptake into the cell. For example, one approach is to delete or lower L-glutamic acid uptake by deleting the gluABCD operon or a part of the operon (EP1038970), etc.

One of the methods for modifying the export of an L-amino acid is to delete or reduce the export of an L-amino acid biosynthetic intermediate, and another method is to strengthen the L-amino acid export. For the former, if the target amino acid is L-glutamic acid, reducing the export of α-ketoglutarate, which is an intermediate in the biosynthesis of L-glutamic acid, by mutating or disrupting the α-ketoglutarate permease gene has been reported (WO01/005959).

To delete or reduce the export of an L-amino acid biosynthetic intermediate, methods for overexpressing genes responsible for L-amino acid export have been reported, for example, producing L-lysine (WO97/23597) or L-arginine using a bacterial strain of a microorganism of the genus *Corynebacterium* with enhanced expression of the L-lysine or L-arginine export gene (LysE) (Journal of Molecular Microbiology Biotechnology (J Mol Microbiol Biotechnol) 1999 November; 1(2):327-36). Furthermore, increasing the expression of the rhtA, B, and C genes (U.S. Pat. No. 6,303, 348), or the yfiK, yahN genes, etc. has been reported as a method for producing L-amino acids in a *Escherichia* bacteria (EP 1013765).

Aside from modifying the L-amino acid biosynthesis pathway and modifying the uptake and export of the L-amino acid as described above, modifying the ability of the bacteria to take up sugar is another example of a method for improving L-amino acid production. For example, the phosphoenolpyruvate: carbohydrate phosphotransferase system (hereinafter, also referred to as PTS: phosphotransferase) is widely known as a transporter which functions to uptake sugar. Furthermore, PTS is classified as a substrate-independent common system EI (encoded by ptsI), HPr (encoded by ptsH), or substrate-specific component EII. Glucose-specific EII is encoded by ptsG and crr, with the crr gene being a part of an operon with ptsH and ptsI. One known method for producing an L-amino acid uses the genus *Escherichia* in which the ptsG gene has been enhanced (WO03/04670), and another method uses the genus *Escherichia* in which the ptsH, ptsI, and crr genes have been enhanced (WO03/04674).

Aside from the glucose PTS mentioned above, the manXYZ genes are known to encode a mannose-specific phosphotransferase (PTS) (Molecular Microbiology (Molecular Microbiology) 1998 27 (2), 369-380), but that the use of a gene encoding mannose PTS for the production of an L-amino acid has not been reported.

SUMMARY OF THE INVENTION

An aspect of the present invention is to provide a bacterial strain which is capable of efficiently producing an L-amino acid and to also provide a method for producing an L-amino acid using the bacterial strain.

In order to resolve the above-mentioned problem, it has been discovered that an L-amino acid can be effectively produced using a microorganism belonging to the family Enterobacteriaceae which has been modified to increase mannose PTS activity.

That is, the present invention is as follows:

It is an aspect of the present invention to provide a method for producing an L-amino acid, comprising culturing in a medium a microorganism of the Enterobacteriaceae family which has the ability to produce an L-amino acid and which has been modified to enhance the mannose PTS activity as compared to a non-modified microorganism, and collecting the L-amino acid from the medium or microorganism.

It is an aspect of the present invention to provide the method described above, wherein said mannose PTS activity is enhanced by increasing expression of the manXYZ gene by a method selected from the group consisting of: increasing the copy number of the gene, modifying an expression regulatory sequence of the gene, and combinations thereof.

It is an aspect of the present invention to provide the method described above, wherein the manXYZ gene encodes a protein selected from the group consisting of:

(A) a protein comprising an amino acid sequence selected from the group consisting of SEQ ID Nos. 2, 3, 4, and combinations thereof, (B) a protein comprising an amino acid sequence selected from the group consisting of SEQ ID Nos. 2, 3, 4, and combinations thereof, wherein said amino acid sequence includes one or more substitutions, deletions, insertions, additions, or inversions of amino acid residues and has mannose PTS activity.

It is an aspect of the present invention to provide the method described above, wherein the manXYZ gene is a DNA selected from the group consisting of:

(a) a DNA comprising the nucleotide sequence of nucleotides 72 to 2767 in SEQ ID No. 1, (b) a DNA encoding a protein having mannose PTS activity which hybridizes with: a sequence complementary to the nucleotide sequence of nucleotides 72 to 2767 in SEQ ID No. 1, or a probe prepared from said nucleotide sequence under stringent conditions.

It is an aspect of the present invention to provide the method described above, wherein the microorganism is a bacterium of the genus *Escherichia* or genus *Pantoea*.

It is an aspect of the present invention to provide the method described above, wherein said L-amino acid is selected from a group consisting of L-lysine, L-threonine, L-glutamic acid, and combinations thereof.

DETAILED DESCRIPTION OF THE PREFERRED EMBODIMENTS

Figure 1:
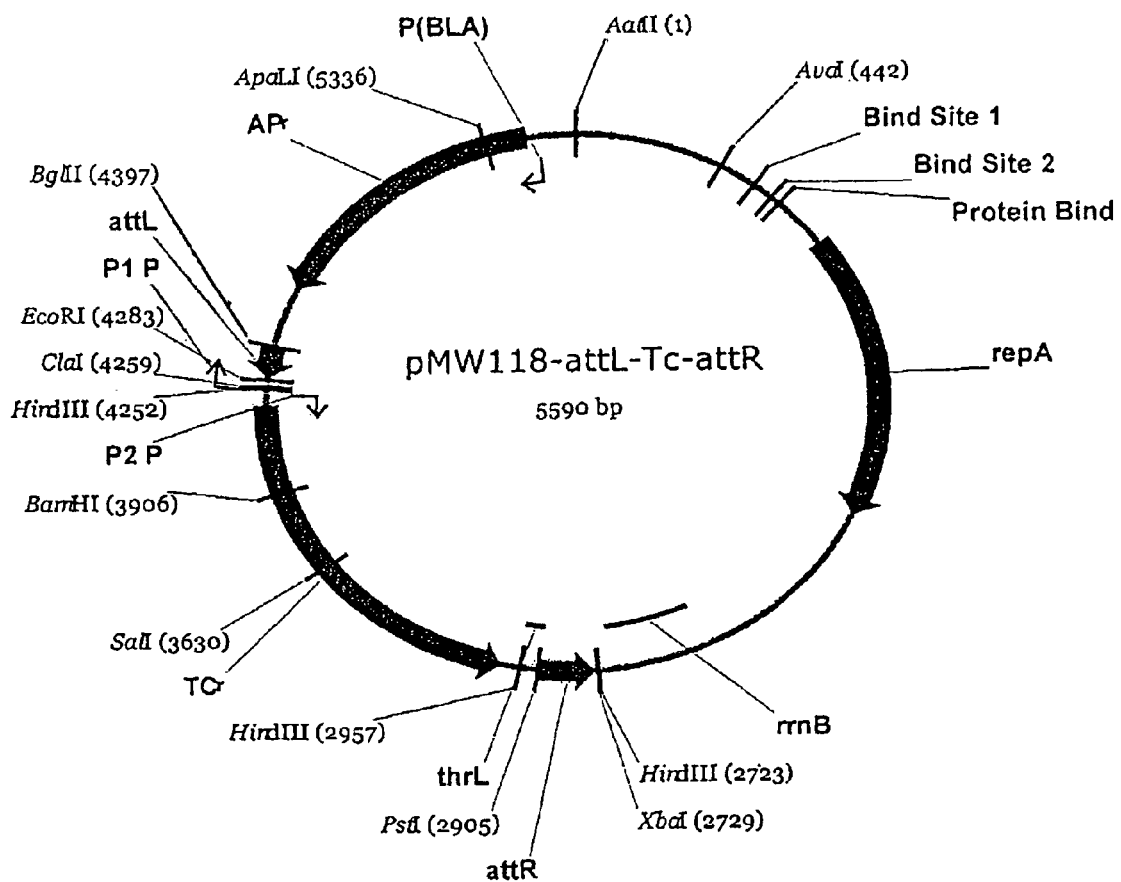
FIG. 1 shows the construction of the plasmid pMW118-attL-Tc-attR
Figure 2:
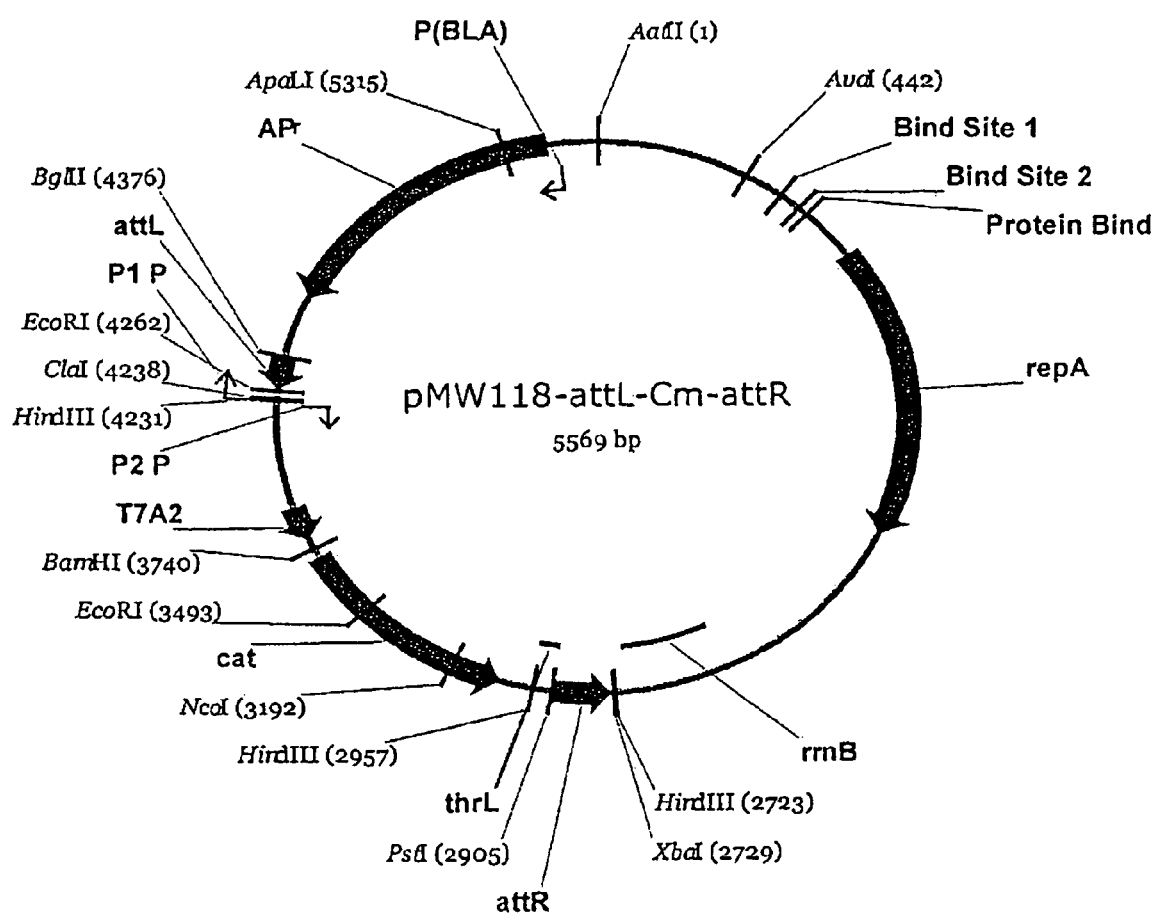
FIG. 2 shows the construction of the plasmid pMW118-attL-Cm-attR.
Figure 3:
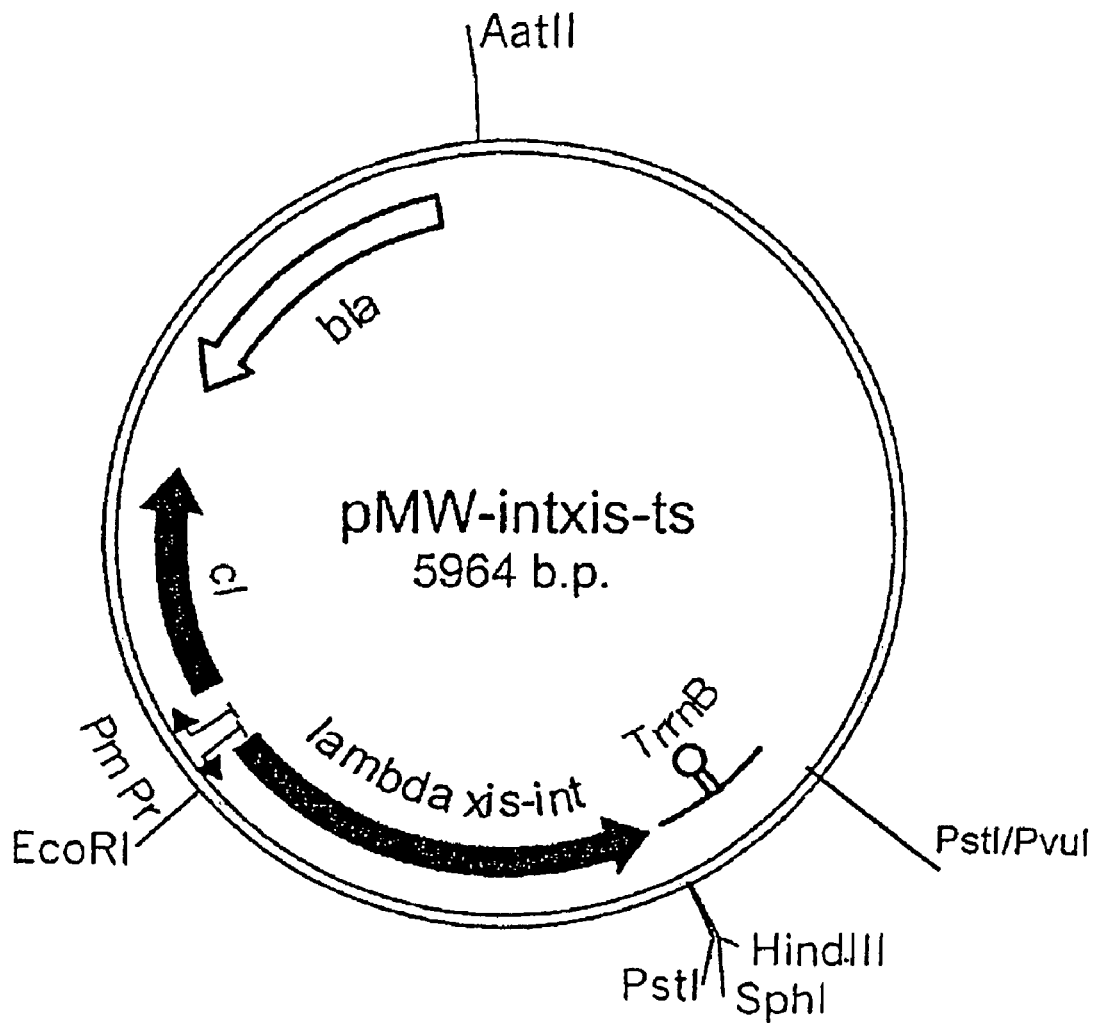
FIG. 3 shows the construction of the plasmid pMW-intxists.

Hereinafter, the present invention will be explained in detail

<1> The Microorganism of the Present Invention

The microorganism of the present invention is of the Enterobacteriaceae family and has an ability to produce an L-amino acid. This microorganism also has been modified to enhance the mannose PTS activity. The phrase "an ability to produce an L-amino acid" means the ability to produce and cause accumulation of an L-amino acid in a medium or in the cells of the microorganism when the microorganism of the present invention is cultured in the medium. The microorganism of the present invention may have the ability to produce multiple L-amino acids. The microorganism inherently possesses the ability to produce an L-amino acid, or may be modified by mutagenesis or recombinant DNA techniques to impart the ability to produce an L-amino acid, such as those described below.

The type of L-amino acid is not particularly limited. Examples of the L-amino acid include the basic L-amino acids such as L-lysine, L-ornithine, L-arginine, L-histidine, and L-citrulline; the aliphatic L-amino acids such as L-isoleucine, L-alanine, L-valine, L-leucine, and L-glycine; the hydroxyl L-amino acids such as L-threonine and L-serine; the cyclic L-amino acids such as L-proline; the aromatic L-amino acids such as L-phenylalanine, L-tyrosine, and L-tryptophan; the sulfur-containing L-amino acids such as L-cysteine, L-cystine, and L-methionine; and the acidic L-amino acid such as L-glutamic acid, L-aspartic acid; the amides of acidic L-amino acids such as L-glutamine, L-asparagine, etc. The microorganism of the present invention may have the ability to produce two or more amino acids.

<1-1> Imparting L-amino Acid-producing Ability

The following examples include a description of the method for imparting L-amino acid-producing ability, along with examples of microorganisms imparted with L-amino acid-producing ability which can be used in the present invention. The microorganisms of the present invention are not limited to these, but can be any as long as they have L-amino acid-producing ability.

There is no particular limitation on the microorganism used in the present invention, as long as it belongs to the family Enterobacteriaceae, such as the genera *Escherichia, Enterobacter, Pantoea, Klebsiella, Serratia, Erwinia, Salmonella, Morganella*, etc., and it has an L-amino acid-producing ability. Specifically, any microorganism belonging to the family Enterobacteriaceae as classified in the NCBI (National Center for Biotechnology Information) database may be used.

It is particularly desirable to use bacteria which belong to the genera *Escherichia, Enterobacter*, or *Pantoea* when modifying parent bacterial species.

The parent bacterial strain of the genus *Escherichia* used to obtain the bacteria of the present invention is not particularly limited, but strains listed by Neidhardt et al., may be used (Neidhardt, F. C. et al., *Escherichia coli* and *Salmonella Typhimurium*, American Society for Microbiology, Washington, D.C., 1029 table 1). One example is *Escherichia coli*. Specific examples of *Escherichia coli* are *Escherichia coli* W3110 (ATCC 27325), *Escherichia coli* MG1655 (ATCC 47076), etc., which are prototypes derived from wild-type strains of K12.

These are available, for example, from the American Type Culture Collection (address: P.O. Box 1549 Manassas, Va. 20108, USA). They are available via use of the accession number given to each bacterial strain (see http:/www.atcc.org). The accession numbers correspond to each bacterial strain, and are listed in the American Type Culture Collection's catalogue.

Examples of bacteria of the genus *Enterobacter* include *Enterobacter agglomerans* and *Enterobacter aerogenes*. An example of a bacterium of the genus *Pantoea* is *Pantoea ananatis*. In recent years, based on 16S rRNA nucleotide sequence analysis, *Enterobacter agglomerans* has on occasion been reclassified as *Pantoea agglomerans, Pantoea ananatis*, and *Pantoea stewartii*. For the present invention, any bacterium classified in the family Enterobacteriaceae, whether *Enterobacter* or *Pantoea*, may be employed. The strains *Pantoea ananatis* AJ13355 (FERM BP-6614), AJ13356 (FERM BP-6615), AJ13601 (FERM BP-7207), or any derivative thereof may be employed to breed *Pantoea ananatis* by genetic engineering methods. When isolated, these strains were identified and deposited as *Enterobacter agglomerans*. As stated above, by analysis using the 16S rRNA nucleotide sequence, these bacteria have been reclassified as *Pantoea ananatis*. For the present invention, any bacterium belonging to the genus *Enterobacter* or *Pantoea* may be used as long as the bacterium is classified in the family Enterobacteriaceae.

The following is a description of methods for imparting an L-amino acid-producing ability to a microorganism which belongs to the Enterobacteriaceae family.

To impart the ability to produce an L-amino acid, an auxotrophic mutant, an analog-resistant strain, or a metabolic regulation mutant can be obtained, or a recombinant strain having enhanced expression of an L-amino acid biosynthesis enzyme can be created. Methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can also be utilized. Here, in the breeding of an L-amino acid-producing bacteria, one or more properties, such as auxotrophic mutation, analog resistance, or metabolic regulation mutation may be imparted. Enhancing the expression of one or more L-amino acid biosynthesis enzymes may also be employed. Furthermore, imparting properties such as auxotrophic mutation, analog resistance, or metabolic regulation mutation may be performed in combination with enhancing the activity of biosynthesis enzymes.

An auxotrophic mutant strain, L-amino acid analog-resistant strain, or metabolic regulation mutant strain with the ability to produce an L-amino acid can be obtained by subjecting a parent or wild-type strain to a conventional mutation treatment, such as treating with X-rays or UV radiation, or treating with a mutagenic agent such as N-methyl-N'-nitro-N-nitrosoguanidine, etc., then selecting those which exhibit an autotrophic mutation, analog resistance, or metabolic regulation mutation and which also have the ability to produce an L-amino acid.

Examples of an L-lysine analog-resistant strain or metabolic regulation mutant include, but are not limited to, the *Escherichia coli* AJ11442 strain (FERM BP-1543, NRRL B-12185, JP56-18596A, and U.S. Pat. No. 4,346,170), and the *Escherichia coli* VL611 strain (EP1016710A), etc. The *Escherichia coli* WC196 strain (WO96/17930) also produces L-lysine. The WC196 strain was bred by imparting AEC (S-(2-aminoethyl)-cysteine) resistance to the W3110 strain derived from *Escherichia coli* K-12. This strain was named *Escherichia coli* AJ13069, and was deposited on Dec. 6, 1994 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14690 and converted to an international deposit under the Budapest Treaty on Sep. 29, 1995, and given Accession No. FERM BP-5252.

L-lysine-producing bacteria can also be constructed by increasing the L-lysine biosynthetic enzyme activity. Examples of genes encoding L-lysine biosynthesis enzymes are the dihydrodipicolinate synthase gene (dapA) (EP 0733710B), aspartokinase gene (lysC) (EP 0733710, U.S. Pat. No. 5,932,453), dihydrodipicolinate reductase gene (dapB), diaminopimelate decarbonylase gene (lysA), diaminopimelate dehydrogenase gene (ddh) (WO96/40934), the phosphoenolpyruvate carboxylase gene (ppc) (JP60-87788A), the aspartate aminotransferase gene (aspC) (JP6-102028A), the diaminopimelate epimerase gene (dapF) (WO00/56858), the aspartate-semialdehyde dehydrogenase gene (asd) (WO00/61723), and other genes of diaminopimelate pathway enzymes; as well as the homoaconitate hydratase gene (JP2000-157276) and other genes of aminoadipate pathway enzymes. The abbreviations for these genes are given in the parentheses following each name.

Furthermore, it is known that the activities of wild-type dihydrodipicolinate synthase (DDPS) and aspartokinase (AK) are inhibited by feedback by L-lysine; therefore, when dapA and lysC are used, it is preferable to use genes encoding mutant dihydrodipicolinate synthase and aspartokinase, respectively, that are resistant to the feedback inhibition by L-lysine (EP 0733710, U.S. Pat. No. 5,932,453).

Examples of the DNA encoding mutant dihydrodipicolinate synthase that is resistant to feedback inhibition by L-lysine include a DNA encoding DDPS having an amino acid sequence wherein the 118th histidine residue is substituted with tyrosine. (U.S. Pat. Nos. 5,661,012 and 6,040,160). Furthermore, examples of the DNA encoding a mutant AK that is resistant to feedback inhibition by L-lysine include a DNA encoding AK having the amino acid sequence wherein the 352-threonine residue is substituted with isoleucine. (U.S. Pat. Nos. 5,661,012 and 6,040,160). These mutant DNAs can be obtained by site-directed mutagenesis using PCR, or the like.

The following is an example of imparting an L-lysine-producing ability by introducing a gene encoding an L-lysine biosynthesis enzyme into the host. That is, recombinant DNA is prepared by ligating the gene fragment that encodes the L-lysine biosynthesis gene with a vector that functions in the host microorganism used in the production of the L-lysine, preferably a multi-copy type vector, and this is used to transform the host. By the transformation, the copy number of the gene encoding the L-lysine biosynthesis enzyme in the host cell increases, enhancing the expression and consequently increasing the enzymatic activity.

The genes encoding the L-lysine biosynthesis enzymes are not particularly limited, as long as they can be expressed in the host microorganism. Examples include genes derived from *Escherichia coli*, and genes derived from coryneform bacteria. Because the total genome sequences of *Escherichia coli* and *Corynebacterium glutamicum* have been determined, it is possible to synthesize primers based on the nucleotide sequence of these genes and obtain these genes using the PCR method in which the chromosomal DNA of a microorganism, such as *Escherichia coli* K12, etc., is used as the template.

In order to clone these genes, plasmids that autonomously replicate in the Enterobacteriaceae can be used. Examples include pBR322, pTWV228 (Takara Bio Inc.), pMW119 (Nippon Gene Co., Ltd.), pUC19, pSTV29 (Takara Bio Inc.), RSF1010 (Gene vol. 75 (2), pp. 271-288, 1989), etc. In addition, a vector of phage DNA may also be used.

To ligate the target gene to the above-mentioned vector, the vector is digested with a restriction enzyme matched to the end of the DNA fragment containing the target gene. The ligation is usually conducted with a ligase such as T4 DNA ligase. Target genes may be present on separate vectors, respectively, or present on the same vector. Typical methods known to those skilled in the art can be employed for digesting and ligating the DNA, as well as for preparing chromosomal DNA, performing PCR, preparing plasmid DNA, transformation, determining the oligonucleotides for use as primers, etc. These methods are described in Sambrook, J., and Russell, D. W. Molecular Cloning A Laboratory Manual/Third Edition. New York: Cold Spring Harbor Laboratory Press (2001), etc. Any method which achieves adequate transformation efficiency may be employed to introduce recombinant DNA that has been prepared as described above into the microorganism. An example includes electroporation (Canadian Journal of Microbiology, 43, 197 (1997)). An example of a plasmid prepared using electroporation is pCABD2, which contains the dapA, dapB, and LysC genes (WO 01/53459).

Enhancing the expression of genes encoding L-lysine biosynthesis enzymes can also be achieved by introducing multiple copies of the target gene into the chromosomal DNA of a microorganism. Multiple copies of the target gene can be introduced into the chromosomal DNA of the microorganism by using a sequence in which multiple copies are present on the chromosomal DNA as a target in homologous recombination. Such site-specific introduction of mutations based on gene substitution using homologous recombination has been described. Methods employing linear DNA or a plasmid containing a temperature-sensitive replication origin have been described (U.S. Pat. Nos. 6,303,383 and 5,616,480). Repetitive DNA and inverted repeats present on the ends of transposable elements can be employed as sequences in which multiple copies are present on chromosomal DNA. An L-lysine biosynthesis gene may be ligated in tandem with a gene which is inherently present on the chromosome, or it may be introduced into a non-essential region on the chromosome or a region of the gene in which the L-lysine yield will be improved if deleted.

Furthermore, as disclosed in U.S. Pat. No. 5,595,889, the target gene may also be located on a transposon, which is then transferred to introduce multiple copies into the chromosomal DNA. With either method, the number of copies of the target gene in the transformant increases, so that the enzymatic activity of the L-lysine biosynthesis increases.

In addition to the above-described genetic amplification, an increase in the L-lysine biosynthesis enzyme activity can be achieved by replacing an expression regulatory sequence of the target gene, such as a promoter etc., with a stronger one (see JP1-215280A). For example, the lac promoter, trp promoter, trc promoter, tac promoter, lambda phage PR promoter, PL promoter, and tet promoter are all known as strong promoters. Substitution with these promoters increases expression of the target gene, thus enhancing enzymatic activity. Examples of strong promoters and methods for evaluating the strength of promoters are described in an article by Goldstein et al. (Prokaryotic promoters in biotechnology. Biotechnol. Annu. Rev., 1995, 1, 105-128), etc.

Increasing L-lysine biosynthesis enzyme activity can also be achieved by modifying an element involved in the regulation of the target gene expression, for example, the operator or repressor (Hamilton et al, J Bacteriol. 1989 September; 171 (9):4617-22). As disclosed in WO 00/18935, a substitution of several bases may be introduced into the −35, −10 region of the promoter of a target gene to modify and strengthen it. Furthermore, substituting several nucleotides into the spacer region between the ribosome binding site (RBS) and the start codon, particularly into the sequence immediately upstream of the start codon, is known to have a strong effect on the mRNA translation efficiency. The expression regulatory regions of the target gene's promoter, etc., can be determined by promoter probe vectors and gene analysis software such as GENETYX, etc. Substitution of expression regulatory sequences can be conducted, for example, in the same manner as in the above-described gene substitution employing temperature-sensitive plasmids. The Red-driven integration method (WO2005/010175) may also used.

Furthermore, in the L-lysine-producing bacteria of the present invention, the activity of an enzyme catalyzing production of a compound other than an L-lysine which branches off from its biosynthesis pathway, or the activity of an enzyme which has a negative effect on the production of L-lysine may be reduced or deleted. These enzymes include homoserine dehydrogenase (thrA), lysine decarboxylase (cadA, lysC), and malic enzyme (sfcA, b2463). The strains with reduced or deficient enzymatic activity are described in WO 95/23864, WO96/17930, WO2005/010175, etc.

To reduce or delete said enzyme activity in a cell, mutagenesis may be performed on the gene which encodes the above-mentioned enzymes, using typical and known methods. This can be achieved, for example, by deleting the gene that encodes the enzyme on the chromosome using genetic recombination, or by modifying the expression regulatory sequence of a promoter or a Shine-Dalgarno (SD) sequence, etc. This can also be achieved by introducing an amino acid substitution (missense mutation) or stop codon (nonsense mutation) in the region encoding the enzyme on the chromosome, by introducing a frameshift mutation to add or delete 1-2 bases, or by deleting a part of the gene or the entire region (Journal of Biological Chemistry 272:8611-8617 (1997); Journal of Antimicrobial Chemotherapy 200 46, 793-796; Biotechnol Prog 1999, 15, 58-64; J. Biological Chemistry vol 272 N0.13 pp 8611-8617). Also, the enzyme activity can be reduced or deleted by constructing a gene that encodes the mutant enzyme in which the encoded region has been deleted and then substituting the wild-type gene on the chromosome with this, by homologous recombination, etc., or introducing a transposon or IS element into said gene.

The following methods may be used to introduce a mutation which reduces or deletes the above-mentioned enzyme activity by genetic recombination. An isolated DNA containing the target gene is mutated so that the resulting mutant gene does not produce an enzyme that functions normally. Then, transforming this into a microorganism which belongs to the family Enterobacteriaceae using the DNA containing the gene, and generating the recombination of the mutant-type gene with a gene on the chromosome. For gene substitution using this kind of homologous recombination, there are methods which employ linear DNA, such as the method called "Red-driven integration" (Proc. Natl. Acad. Sci. USA, 2000, vol. 97, No. 12, pp. 6640-6645), or by combining the Red-driven integration method and the λ phage excisive system (J. Bacteriol. 2002 September; 184 (18): 5200-3, Interactions between integrase and excisionase in the phage lambda excisive nucleoprotein complex. Cho E H, Gumport R I, Gardner J F) (see WO2005/010175), etc.; and there are methods which employ a plasmid containing a temperature-sensitive replication origin (Proc. Natl. Acad. Sci. USA, 2000, vol. 97, No. 12, pp. 6640-6645, U.S. Pat. No. 6,303,383, or 5,616,480). Such site-specific introduction of mutations via gene substitution using homologous recombination as described above may also be performed using a plasmid which does not have replication ability in the host.

The above-mentioned method for increasing the enzyme activity involving L-lysine biosynthesis and the method for lowering the enzyme activity may likewise be used in breeding other L-amino acid-producing bacteria. The following is a description of methods for breeding other L-amino acid bacteria.

As the L-glutamic acid-producing bacteria used in the present invention, there is, for example, a microorganism which belongs to the family Enterobacteriaceae which has been modified to increase the expression of a gene encoding an enzyme that is involved in L-glutamic acid biosynthesis. The enzymes involved in L-glutamic acid biosynthesis include glutamate dehydrogenase (gdh), glutamine synthetase (gltAB), glutamate synthase (glnA), isocitrate dehydrogenase (icd), aconitate hydratase (acn), citrate synthase (gltA), phosphoenolpyruvate carboxylase (ppc), pyruvate carboxylase (pycA), pyruvate dehydrogenase (pdhA), pyruvate kinase (pykA), phosphoenolpyruvate synthase (pps), enolase (eno), phosphoglucomutase (pgm), phosphoglycerate kinase (pgk), glyceraldehyde-3-phosphate dehydrogenase (gpd), triose phosphate isomerase (tpi), fructose-bisphosphate aldolase (fba), phosphofructokinase (pfk), glucosephosphate isomerase (gpi), etc. Of these enzymes, citrate synthase, phosphoenolpyruvate carboxylase, glutamate dehydrogenase, and combinations thereof are preferable, and the use of all three is more preferable.

Examples of microorganisms belonging to the family Enterobacteriaceae which have been modified to enhance the expression of the citrate synthase gene, phosphoenolpyruvate carboxylase gene, and/or glutamate dehydrogenase gene using the methods described above are given in U.S. Pat. Nos. 6,197,559 & 6,331,419, EP0999282, and WO2006/051660.

Furthermore, microorganisms belonging to the family Enterobacteriaceae which have been modified to increase the activity of either 6-phosphogluconate dehydratase or 2-keto-3-deoxy-6-phosphogluconate aldolase, or both, may also be used (EP1352966B).

The microorganisms of the family Enterobacteriaceae having the ability to produce an L-glutamic acid which may be used include a bacterium in which the activity of an enzyme that catalyzes production of a compound other than L-glutamic acid, but which branches off from the biosynthesis pathway of L-glutamic acid, has been reduced or lowered. Examples of such enzymes include 2-oxoglutarate dehydrogenase (sucA), isocitrate lyase (aceA), acetohydroxy acid synthase (ilvG), acetolactate synthase (ilvN), formate acetyltransferase (pflB), lactate dehydrogenase (ldh), glutamate decarboxylase (gadA), and 1-pyrroline dehydrogenase (putA), etc. Of these, it is especially preferable to reduce or delete the activity of 2-oxoglutarate dehydrogenase.

Methods for deleting or reducing the activity of 2-oxoglutarate dehydrogenase in a microorganism belonging to the family Enterobacteriaceae are described in U.S. Pat. No. 5,573,945, U.S. Pat. No. 6,197,559, and U.S. Pat. No. 6,331,419. Examples of microorganisms belonging to the family Enterobacteriaceae wherein the activity of 2-oxoglutarate dehydrogenase has been deleted or reduced include the following:

*Pantoea ananatis* AJ13601 (FERM BP-7207)
*Klebsiella planticola* AJ13410 strain (FERM BP-6617)
*Escherichia coli* AJ12949 (FERM BP-4881), and others.

The AJ12949 strain has reduced α-ketoglutarate dehydrogenase activity, and was deposited on Dec. 28, 1993 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14039 and converted to an international deposit under the Budapest Treaty on Nov. 11, 1994, and given Accession No. FERM BP-4881.

The L-tryptophan-producing bacteria preferably used in the present invention are bacteria in which the activity of one or more of the following enzymes, i.e., anthranilate synthase (trpE), phosphoglycerate dehydrogenase (serA), or tryptophan synthase (trpAB) has been enhanced. Since anthranilate synthase and phosphoglycerate dehydrogenase both are subject to feedback inhibition by L-tryptophan and L-serine, the activities of these enzymes can be increased by retaining the desensitizing mutant enzyme. (U.S. Pat. Nos. 5,618,716, 6,180,373). For instance, it is possible to obtain bacteria which have a desensitizing enzyme by mutating the anthranilate synthase gene (trpE) and/or the phosphoglycerate dehydrogenase gene (serA) to prevent feedback inhibition, then introducing the mutant gene into a microorganism belonging to the family Enterobacteriaceae. A specific example of this kind of bacteria is *Escherichia coli* SV164 which retains desensitized anthranilate synthase and which has been transformed with plasmid pGH5 having a mutated serA that encodes desensitized phosphoglycerate dehydrogenase (WO94/08301).

Bacteria transformed with recombinant DNA containing a tryptophan operon are also preferable L-tryptophan-producing bacteria. A specific example is *Escherichia coli* transformed with a tryptophan operon containing a gene encoding desensitized anthranilate synthase (trpAB) (Japanese Patent Application Publication No. JP57-71397, Japanese Patent Application Publication No. JP 62-244382, U.S. Pat. No. 4,371,614). Furthermore, in the tryptophan operon, it is possible to enhance the ability to produce L-tryptophan by increasing the expression of the gene (trpBA) encoding tryptophan synthase. Tryptophan synthase contains α and β subunits that are encoded by trpA and trpB, respectively. (WO2005/103275)

Examples of L-tryptophan-producing bacteria are *Escherichia coli* AGX17 (pGX44) [NRRL B-12263], which requires L-phenylalanine and L-tyrosine for growth, and AGX6 (pGX50) aroP [NRRL B-12264], which retains plasmid pGX50 containing a tryptophan operon (see U.S. Pat. No. 4,371,614).

A strain with a deficient tryptophan operon repressor (trpR), and a strain with a mutant trpT are also desirable L-tryptophan-producing bacteria. (U.S. Pat. No. 4,371,614 WO2005/056776).

Another preferable L-tryptophan-producing bacterium is the bacterium in which malate synthase (aceB), isocitrate lyase (aceA), and the isocitrate dehydrogenase/phosphatase (icl) operon (ace operon) are structurally expressed, or the expression of said operon has been enhanced (WO2005/103275).

L-tryptophan, L-phenylalanine, and L-tyrosine are all aromatic amino acids and share a biosynthesis system. Examples of genes encoding biosynthesis enzymes of aromatic amino acids include deoxyarabino-heptulosonate phosphate synthase (aroG), 3-dehydroquinate synthase (aroB), shikimate dehydratase, shikimate kinase (aroL), 5-enolpyruvylshikimate[-]3-phosphate synthase (aroA), and chorismate synthase (aroC) (European Patent Application Publication No. 763127). Therefore, by placing multiple copies of the genes encoding these enzymes onto a plasmid or genome, the aromatic amino acid-producing ability can be improved. It is known that these genes are controlled by a tyrosine repressor (tyrR), so the biosynthesis enzyme activity of an aromatic amino acid may also be increased by deleting the tyrR gene (EP763127).

The L-threonine-producing bacteria are preferably microorganisms belonging to the family Enterobacteriaceae wherein the L-threonine biosynthesis enzymes have been enhanced. Examples of genes encoding L-threonine biosynthesis enzymes include the aspartokinase III gene (lysC), the aspartate-semialdehyde dehydrogenase gene (asd), the aspartokinase I gene encoding the thr operon (thrA), the homoserine kinase gene (thrB), and the threonine synthase gene (thrC). The abbreviations for these genes are given in parentheses following their names. One or more of these genes may be introduced. The L-threonine biosynthesis gene may be introduced into a bacterium of the genus *Escherichia* wherein threonine degradation has been suppressed. Examples of bacteria of the genus *Escherichia* wherein threonine degradation has been suppressed include the TDH6 strain wherein the threonine dehydrogenase activity has been deleted (Japanese Patent Application Publication No. 2001-346578), and so forth.

Activities of some of the L-threonine biosynthesis enzymes are suppressed by the L-threonine that is produced. Therefore, in order to construct an L-threonine-producing bacterium, it is preferable to modify the L-threonine biosynthesis enzyme so that the enzyme is not subject to feedback inhibition by L-threonine. The above-mentioned thrA, thrB, and thrC genes make up the threonine operon, which is in the form of an attenuator structure. The expression of the threonine operon is subject to inhibition by isoleucine and threonine present in the culture, and the expression is attenuated. This modification of the theonine operon can be achieved by removing the leader sequence in the attenuation region or the attenuator. (WO 02/26993; Biotechnology Letters Vol. 24, No. 21, November 2002; WO2005/049808).

A native promoter is located on the threonine operon, and may be substituted with a non-native promoter (WO 98/04715). Alternatively, a threonine operon may be constructed so that the expression of the gene involved in threonine biosynthesis is controlled by a lambda phage repressor and promoter. (EP0593792). Also, to prevent feedback inhibition by L-threonine, modification of the bacteria of the genus *Escherichia* can also be obtained by selecting an α-amino-β-hydroxyvaleric acid (AHV) resistant bacteria strain (JP45026708B).

It is preferred that the copy number of threonine operon which is modified to prevent feedback inhibition by L-threonine is increased in the host or is ligated to a strong promoter. In addition to amplifying the copy number of the gene using a plasmid, the copy number of the gene can be increased by introducing the threonine operon onto the chromosome using a transposon, Mu-phage, etc.

For the aspartokinase III gene (lysC), it is desirable to use a gene modified to prevent feedback inhibition by L-lysine. A lysC gene which has been modified to prevent feedback inhibition can be obtained using the method described in the U.S. Pat. No. 5,932,453.

Aside from the L-threonine biosynthesis enzyme, it is desirable to strengthen genes involved in the glycolytic system, TCA cycle, and respiratory chain, a gene which controls gene expression, and a gene which induces uptake of sugar. Examples of these genes which are effective in L-threonine production include the transhydrogenase gene (pntAB) (EP733712), phosphoenolpyruvate carboxylase gene (ppc) (WO 95/06114), the phosphoenolpyruvate synthase gene (pps) (EP 877090), and the pyruvate carboxylase gene in the coryneform bacteria or *Bacillus* bacteria (WO99/18228, EP1092776).

It is also preferable to enhance the expression of a gene that imparts resistance to L-threonine and a gene that imparts resistance to L-homoserine, or to impart both L-threonine resistance and L-homoserine resistance to the host. Examples of such genes are the rhtA gene (Res Microbiol. 2003 March; 154 (2): 123-35), the rhtB gene (EP0994190), the rhtC gene (EP1013765), the yfiK gene, and the yeaS gene (EP1016710). To impart L-threonine resistance to a host, refer to European Patent Application Publication No. 0994190 and WO 90/04636.

Another example of an L-threonine-producing bacterium is the *Escherichia coli* VKPM B-3996 strain (U.S. Pat. No. 5,175,107). This VKPM B-3996 strain was deposited on Nov. 19, 1987, under Accession No. VKPM B-3996, at the Russian National Collection of Industrial Microorganisms (VKPM), GNII Genetika. In addition, the VKPM B-3996 strain retains plasmid pVIC40 (WO90/04636) obtained by inserting a threonine biosynthesis gene (threonine operon: thrABC) into a wide-host vector plasmid pAY32 including a streptomycin-resistant marker (Chistorerdov, A. Y., Tsygankov, Y. D., Plasmid, 1986, 16, 161-167). In this pVIC40, the feedback inhibition by the L-threonine of the aspartokinase I-homoserine dehydrogenase I that the thrA in the threonine operon encodes has been desensitized.

A further example is the *Escherichia coli* B-5318 strain (see European Patent No. 0593792). The B-5318 strain was deposited under Accession No. VKPM B-5318 at the Russian National Collection of Industrial Microorganisms (VKPM), GNII Genetika (Russia, 117545 Moscow, 1 Dorozhny Proezd, 1) on May 3, 1990. This VKPM B-5318 strain is an isoleucine non-auxotrophic strain, and retains recombinant plasmid DNA constructed in such a way that the gene involved in threonine biosynthesis, i.e., the threonine operon wherein the attenuator region and the native transcriptional regulatory region has been deleted, is located downstream of the lambda phage temperature-sensitive CI repressor, PR promoter, and the N-terminus of Cro protein of lambda phage, and expression of the gene involved in the threonine biosynthesis is controlled by the lambda phage repressor and promoter.

Examples of preferred L-histidine-producing strains include the *Escherichia coli* FERM P-5038 and 5048 strains harboring vectors in which genetic information involved in L-histidine biosynthesis have been incorporated (JP56-005099A), a bacterial strain into which the amino acid export gene Rht has been introduced (EP1016710), and the *Escherichia coli* 80 strain which has resistance to sulfaguanidine, D, L-1,2,4-triazole-3-alanine, and streptomycin (VKPM B-7270, Russian Patent Publication No. 2119536), etc.

Microorganisms in which expression of the gene encoding the L-histidine biosynthesis pathway enzyme may be used to produce L-histidine. Examples of L-histidine biosynthesis enzymes are ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide Isomerase (hisA), amidotransferase (hisH), histidinol phosphate aminotransferase gene (hisC), histidinol phosphatase gene (hisB), and histidinol dehydrogenase gene (hisD), etc.

The preferred L-cysteine-producing bacteria of the present invention are bacteria in which the activity of the cystathionine β-lyase has been reduced (JP2003-169668), and bacteria of the genus *Escherichia* that retain serine acetyltransferase with reduced feedback inhibition by L-cysteine (JP11-155571).

The preferred L-proline-producing bacteria of the present invention include *Escherichia coli* 702 (VKPMB-8011) which is resistant to 3,4-dehydroxyproline and azetidine-2-carboxylate, and 702 ilvA (VKPMB-8012 strain), which is deficient in ilvA, and is derived from 702 (JP 2002-300874A).

Examples of L-phenylalanine-producing bacteria include AJ12739 (tyrA::Tn10, tyrR) (VKPM B-8197) which is deficient in tyrA and tyrR, and strains with amplified genes encoding phenylalanine export proteins, such as yddG and yedA.

Examples of L-arginine-producing bacteria include *Escherichia coli* mutant strains which are resistant to α-methylmethionine, p-fluorophenylalanine, D-arginine, arginine hydroxamic acid, S-(2-aminoethyl)-cysteine, α-methyleserine, β-2-thienylalanine, or sulfaguanidine (JP56-106598), etc. The *Escherichia coli* 237 strain is an L-arginine-producing bacterium that has a mutant which is resistant to feedback inhibition by L-arginine and that retains highly active N-acetyl glutamate synthase, and it is also a preferable L-arginine-producing strain. (EP1170361B). This strain, numbered VKPM B-7925, was deposited with the Russian National Collection of Industrial Microorganisms (VKPM), GNII Genetika on Apr. 10, 2000, and converted to an international deposit under the Budapest Treaty on May 18, 2001. The *Escherichia coli* 382 strain, which is a derivative of the 237 strain and is an L-arginine-producing bacterium with improved acetic acid assimilating ability, may also be used (U.S. Pat. No. 6,841,365). The *Escherichia coli* 382 strain, numbered VKPM B-7926, was deposited with the Russian National Collection of Industrial Microorganisms (VKPM) on Apr. 10, 2000.

Also, as the microorganisms having L-arginine-producing ability, microorganisms with improved expression of genes encoding enzymes involved in L-arginine biosynthesis may be used. Examples of L-arginine biosynthesis enzymes include N-acetyl glutamate synthase (argA), N-acetyl-glutamyl-phosphate reductase (argC), ornithine acetyltransferase (argJ), N-acetyl glutamate kinase (argB), acetyl ornithine transaminase (argD), acetyl ornithine deacetylase (argE), ornithine carbamoyl transferase (argF), argininosuccinate synthase (argG), argininosuccinate lyase (argH), and carbamoyl phosphate synthase (carAB), and combinations thereof. After each enzyme name, the name of the gene encoding it is given in parentheses. It is desirable to employ a mutation of the N-acetyl glutamate synthase gene (argA) in which L-arginine feedback inhibition has been removed by substitution of the amino acid sequence corresponding to positions 15 to 19 in the wild-type (EP EP1170361).

The L-leucine-producing bacteria which may be used include a bacterium of the genus *Escherichia coli* in which the branched-chain amino-acid transaminase encoded by the ilvE gene has been inactivated and the activity of the aromatic amino acid transaminase encoded by the tyrB gene has been enhanced (EP1375655A), the *Escherichia coli* H-9068 strain (ATCC21530) which is resistant to 4-azaleucine or 5,5,5-trifluoroleucine, the *Escherichia coli* H-9070 strain (FERM BP-4704), the *Escherichia coli* H-9072 strain (FERM BP-4706) (U.S. Pat. No. 5,744,331), the *Escherichia coli* strain in which the isopropylmalate synthase feedback inhibition by L-leucine has been desensitized (European Patent No. 1067191), the *Escherichia coli* AJ11478 strain which is resistant to β-2 thienylalanine and β-hydroxyleucine (U.S. Pat. No. 5,763,231), and so on.

L-isoleucine-producing bacteria include a 6-dimethyl aminopurine-resistant *Escherichia coli* mutant strain (JP 5-304969A), L-isoleucine hydroxamate-resistant *Escherichia coli* mutant strain (JP5-130882A), thiaisoleucine-resistant *Escherichia coli* mutant strain (JP5-130882A), DL-ethionine-resistant *Escherichia coli* mutant strain (JP5-130882A), and arginine hydroxamate-resistant mutant strain (JP5-130882A), all of which have L-isoleucine-producing ability. Examples of recombinant bacteria of the genus *Escherichia* are bacterial strains in which the expression of the genes encoding the L-isoleucine biosynthesis enzymes threonine deaminase or acetohydroxy acid synthase have been increased (JP2-458A, JP2-42988A, JP 8-47397A), etc.

Examples of parent strains for deriving L-valine-producing bacteria of the present invention include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by L-valine. Furthermore, the ilvA gene in the operon is desirably disrupted to decrease threonine deaminase activity.

Examples of parent strains for deriving L-valine-producing bacteria of the present invention include mutants having a mutation in the amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking H+-ATPase can also be used as parent strains (WO96/06926).

Aside from a gene which encodes a native biosynthesis enzyme, a gene which is involved in sugar uptake, sugar metabolism (glycolytic system), and energy metabolism may be enhanced in the L-amino acid-producing bacteria of the present invention.

Examples of the genes involved in sugar metabolism are genes which encode glycolytic enzymes or proteins which uptake sugar, such as genes encoding the glucose-6-phosphate isomerase gene (pgi; WO01/02542), the phosphoenolpyruvate synthase gene (pps), the phosphoglucomutase gene (pgm; WO03/04598), the fructose-bisphosphate aldolase gene (fba; WO03/04664), the pyruvate kinase gene (pykF; WO03/008609), the transaldolase gene (talB; WO03/008611), the fumarase gene (fum; WO01/02545), the phosphoenolpyruvate synthase gene (pps; EP877090), the non-PTS sucrose uptake systems gene (csc; EP149911), and the sucrose-assimilating genes (scrAB operon; WO90/04636).

Examples of the genes involved in energy metabolism include the transhydrogenase gene (pntAB; U.S. Pat. No. 5,830,716) and the cytochrome bo type oxidase gene (cyoABCD; EP1070376).

<1-2> Method for Increasing the Activity of Mannose PTS

The microorganism of the present invention can be obtained by modifying a microorganism which has the ability to produce an L-amino acid and which belongs to the Enterobacteriaceae family, as described above, so as to increase the enzymatic activity of the mannose PTS. However, the ability to produce an L-amino acid may be imparted after modification to increase the enzymatic activity of the mannose PTS. The mannose PTS in the present invention means the activity of taking up sugar into the cytoplasm while, at the same time, transferring the phosphate group in phosphoenolpyruvate (hereinafter, referred to as PEP) to the sugar. As used herein, sugar means mannose, but may also be glucose, fructose, or amino sugar. (Molecular Microbiology (1998) 27(2), 369-380).

An increase in the enzymatic activity of the mannose PTS can be confirmed by in vitro measurement of the phosphorylating activity using the method of Chen et al. (Biochemistry 1998 37:8714-8723) (EC 2.7.1.69). Enhancing or increasing the expression of the gene encoding the mannose PTS as compared to the parent strain, for example, a wild-type strain or non-modified strain, can also be confirmed by comparing the amount of mRNA with that in the wild-type or non-modified strain. Northern hybridization and RT-PCR can also be used to confirm expression (Molecular Cloning (Cold Spring Harbor Laboratory Press, Cold Spring Harbor (USA), 2001)). The degree of increase in enzymatic activity is not limited as long as the activity is increased as compared to that in the wild or non-modified strain, but it is desirable, for example, to increase the activity by 1.5 or more times, preferably 2 or more times, or more preferably 3 or more times than that of the wild-type or non-modified strain. An increase in the enzymatic activity can be confirmed if the amount of the target protein is increased relative to that in the non-modified or wild-type strain. This can be detected, for instance, by Western blot using an antibody. (Molecular Cloning (Cold Spring Harbor Laboratory Press, Cold spring Harbor (USA), 2001)).

An increase in the enzymatic activity of the mannose PTS can be achieved by modifying expression of the manX, manY, and manZ genes which encode the mannose PTS (described later). This may be an increase in the expression of the endogenous manX, manY, and manZ genes by modifying the expression regulatory region, including the promoter; or by increasing the expression of the exogenous manX, manY, and manZ genes by introducing a plasmid containing the manX, manY, and manZ genes, by increasing the copy number by amplifying the manX, manY, and manZ genes on the chromosome, etc. The manX, manY, and manZ genes form an operon structure (hereinafter, referred to as "manXYZ operon"); and increasing enzyme activity can be more effectively achieved by modifying the expression regulatory region of the man XYZ operon by substituting it with a stronger one, and by increasing the number of copies of the manXYZ operon.

Total genome sequences of *Escherichia coli* have been determined (Science 277:1453-1462 (1997)), and each gene's function and Genbank Accession Nos. are as follows:

TABLE 1

| Gene | Altenative gene names | description | EC No. | SEQ ID: DNA | SEQ ID: Amino acid | Genbank Accession No |
|---|---|---|---|---|---|---|
| manX | gptB, mpt, ptsL, ptsM, ptsX | PTS enzyme IIAB, mannose-specific | EC: 2.7.1.69 | SEQID: No. 1 72-1040 | SEQ ID: No. 2 | NP_416331 |
| manY | pel, ptsM, ptsP, ptsX | PTS system, mannose-specific IIC component | | SEQID: No. 1 1106-1903 | SEQ ID: No. 3 | NP_416332 |
| manZ | gptB, mpt, ptsM, ptsX | PTS enzyme IID, mannose-specific | | SEQID: No. 1 1910-2767 | SEQ ID: No. 4 | NP_416333 |

The manX, manY, and manZ genes of the present invention include the manX, manY, and manZ genes of the bacteria of the genus *Escherichia* and their homologs. For example, the manX gene from *Escherichia coli* encodes a protein with an amino acid sequence of SEQ ID No. 2, the manY gene encodes a protein with an amino acid sequence of SEQ ID No. 3, and the manZ gene encodes a protein with an amino acid sequence of SEQ ID No. 4. The coding region of SEQ ID No. 1 and the Genbank Accession Nos. of the manX, Y, Z genes derived from *Escherichia Coli* MG1655 are shown in Table 1.

The homologs of the manX, manY, and manZ genes are genes that are derived from other microorganisms, which have high similarity in structure to the manX, manY, and manZ genes of the bacteria of the genus *Escherichia*, and which improve the ability to produce L-amino acid and exhibit mannose PTS activity when introduced into a host. Examples of manX, Y, Z homologs are the manX, manY, and manZ genes of the genera *Salmonella*, *Shigella*, and *Yersinia* registered at Genbank. Furthermore, based on the homology with the genes given in the above examples, these manX, Y, Z genes may be cloned from coryneform bacteria, such as *Corynebacterium glutamicum*, *Brevibacterium lactofermentum*, etc.; the bacteria of the genus *Pseudomonas*, such as *Pseudomonas aeruginosa*, etc.; the bacteria of the genus *Mycobacterium*, such as *Mycobacterium tuberculosis*, etc.; and the bacteria of the genus *Bacillus*. As shown in Table 1, different gene names are acceptable as long as they are highly homologous with the manXYZ of the bacteria of the genus *Escherichia*. For example, a gene that encodes a mannose PTS may be cloned using synthetic oligonucleotide SEQ ID Nos. 5 and 6.

The genes encoding the mannose PTS are not limited to the wild-type genes, and as long as the function of the encoded mannose PTS protein, i.e., mannose PTS activity, is not impared, they can also be mutants or artificially modified genes which encode a protein including a sequence containing one or several amino acid substitutions, deletions, insertions, additions, or the like at one or multiple positions in the amino acid sequences of SEQ ID Nos. 2, 3, and 4. Here, the term "several" varies with the type and position of the amino acid residue in the stereostructure of the protein; specifically, it means 1 to 20, preferably 1 to 10, and more preferably 1 to 5. The above substitutions, deletions, insertions, or additions of one or several amino acids are conservative mutations that preserve the mannose PTS activity. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Preferred conservative substitutions also include substitution of Ala by Ser or Thr; the substitution of Arg by Gln, His, or Lys; the substitution of Asn by Glu, Gln, Lys, His, or Asp; the substitution of Asp by Asn, Glu, or Gln; the substitution of Cys by Ser or Ala; the substitution of Gln by Asn, Glu, Lys, His, Asp, or Arg; the substitution of Gly, Asn, Gln, Lys, or Asp; the substitution of Gly by Pro; the substitution of His by Asn, Lys, Gln, Arg, or Tyr; the substitution of Ile by Leu, Met, Val, or Phe; the substitution of Leu by Ile, Met, Val, or Phe; the substitution of Lys by Asn, Glu, Gln, His, or Arg; the substitution of Met by Ile, Leu, Val, or Phe; the substitution of Phe by Trp, Tyr, Met, Ile, or Leu; the substitution of Ser by Thr or Ala; the substitution of Thr by Ser or Ala; the substitution of Trp by Phe or Tyr; the substitution of Tyr by His, Phe, or Trp; and the substitution of Val by Met, Ile, or Leu. Substitutions, deletions, insertions, additions, or inversions and the like of the amino acids described above include naturally occurring mutations (mutant or variant) due to the differences in species, or individual differences of microorganisms that retain genes encoding a mannose PTS. Such genes can be obtained by modifying, using, for instance, the site-specific mutation method, the nucleotide sequence shown in SEQ ID No. 1, so that the site-specific amino acid residue in the protein encoded includes substitutions, deletions, insertions, or additions.

Moreover, the genes that encode the mannose PTS encode a protein having 80% or above, preferably 90% or above, more preferably 95% or above, even more preferably 97% or above, homology with the amino acid sequences of SEQ Nos. 2, 3, and 4. Since the degenerate code properties of a gene vary with the host into which the gene is introduced, a gene substituted with codons that are more readily utilized by the host is desirable. Likewise, as long as the gene encoding the mannose PTS encodes a protein with the function of the mannose PTS, the N terminal or C terminal of the gene may be extended or removed. For example, the number of amino acids which can be extended or removed may be 50 or less, preferably 20 or less, more preferably 10 or less, and even more preferably 5 or less. More specifically, for a gene with from 50 to 5 amino acids extended or removed from either end of SEQ ID No s. 2, 3, and 4 may be used.

Also, a variant of the gene can be obtained by the following conventional mutation treatments. For example, a gene having a nucleotide sequence of nucleotides 72 to 2767 of SEQ ID No. 1, may be mutated in vitro using hydroxylamine, etc. Another method employs treating the *Escherichia* bacteria with a typical mutation treatment, such as ultraviolet light or a mutation agent, such as N-methyl-N'-nitro-N-nitrosoguanidine (NTG) or Ethyl Methyl Sulfonate (EMS). Whether or not these genes encode a protein that has mannose PTS activity can be confirmed, for example, by expressing these genes in the appropriate cells, and investigating if the ability to uptake mannose has been increased, or investigating the phosphorylating activity in vitro employing the method of Chen et al. (Biochemistry 1998 37:8714-8723).

The genes that encode the mannose PTS can also be DNA that hybridizes under stringent conditions with nucleotide sequences complementary to nucleotide sequences of nos. 72 to 2767 of SEQ ID No. 1, or with a probe prepared from these sequences. Here, the term "stringent conditions" refers to conditions under which so-called specific hybrids are formed and nonspecific hybrids are not formed. Although it is difficult to clearly express such conditions in numbers, these can be exemplified as conditions under which highly homologous fragments of DNA, for example, DNA having homology no less than 80%, 90%, or 95%, hybridize with each other and DNA having homology lower than the above do not hybridize with each other. Alternatively, stringent conditions are exemplified by conditions of typical Southern hybridization washing conditions, which are to wash once or preferably two to three times at a temperature and salt concentration corresponding to 60° C., 1×SSC, 0.1% SDS, preferably 0.1×SSC, 0.1% SDS, and more preferably, 68° C., 0.1×SSC, 0.1% SDS.

DNA containing the nucleotide sequence of numbers 72 to 2767 of SEQ ID No. 1, or a part thereof may also be used as the probe. Such a probe can be prepared using PCR wherein a DNA fragment containing a nucleotide sequence of SEQ ID No. 1 is used as the template, and an oligonucleotide prepared based on the nucleotide sequence of SEQ ID No. 1 as the primer. For example, when using an approx. 300 bp long DNA fragment as the probe, the hybridization washing conditions are 50° C., 2×SSC, and 0.1% SDS.

To enhance the expression of the gene encoding the mannose PTS, genetic recombination techniques, for example, can be employed to increase the number of copies of the above-mentioned gene that encodes the mannose PTS in the cell. For example, a DNA fragment containing the gene encoding the mannose PTS is ligated with a vector, preferably a multicopy type vector, which functions in the host microorganism to prepare the recombinant DNA, which is then introduced into the microorganism to transform it.

When the manX, Y, Z genes of *Escherichia coli* are used, they can be obtained using PCR (PCR: polymerase chain reaction; see White, T. J. et al., Trends Genet. 5, 185 (1989)) in which the chromosomal DNA of *Escherichia coli* is the template, and primers are prepared based on the nucleotide sequence of SEQ ID No. 1, for example, the primers shown in SEQ ID Nos. 5 and 6. The genes encoding the mannose PTS of other microorganisms belonging to the family Enterobacteriaceae can also be obtained from the known manX, Y, and Z genes in those microorganisms or the manX, Y, and Z genes in microorganisms of other species, or chromosomal DNA or a chromosomal DNA library from those microorganisms, using PCR wherein the primers are prepared based on the sequence information of the mannose PTS protein, or the hybridization method wherein the probe is prepared based on the above-mentioned sequence information. Incidentally, chromosomal DNA can be prepared from DNA donor microorganisms. For example, Saito and Miura's method, etc., (see H. Saito and K. Miura, Biochem. Biophys. Acta, 72, 619 (1963), Seibutsu Kogaku Jikkensho [Bioengineering Experiments], edited by The Society of Biotechnology, Japan, pp. 97-98, Baifukan, 1992), may be used.

Next, the recombinant DNA is prepared by ligating the gene(s) encoding the mannose PTS amplified by PCR using a vector DNA capable of functioning in the chosen host microorganism, for example, one which is autonomously replicable in the cells of the host microorganism. Examples of autonomously replicable vectors in cells of *Escherichia Coli* include pUC19, pUC18, pHSG299, pHSG399, pHSG398, pACYC184, (pHSG and pACYC are available from Takara Bio Inc.), RSF1010, pBR322, pMW219 (pMW is available from Nippon Gene Co., Ltd.), pSTV29 (available from Takara Bio Inc.), etc.

Recombinant DNA prepared as described above may be introduced to a microorganism in accordance with any of the transformation methods which have been reported to date. For example, the permeability of the DNA can be increased by treating the recipient bacteria with calcium chloride, as reported with regards to *Escherichia coli* K-12 (Mandel, M. and Higa, A., J. Mol. Biol., 53, 159 (1970)). Another method is to introduce the DNA after preparing competent cells from the cells at the growth phase, as reported with regards to *Bacillus subtilis* (Duncan, C. H., Wilson, G. A. and Young, F. E., Gene, 1, 153 (1977)). Also, in relation to *Bacillus subtilis*, actinomycete and yeast, the host microorganism can be changed into the protoplast or spheroplast state that can easily uptake the recombinant DNA, which is then introduced into the DNA recipient bacteria (Chang, S, and Choen, S, N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75 1929 (1978)). The cornyneform group of bacteria can also be transformed using the electric pulse method (Sugimoto, et al., Japanese Patent Application Publication No. Hei 2-207791).

The copy number of the gene encoding the mannose PTS can be increased by introducing multiple copies of the gene encoding the mannose PTS as described above into the chromosomal DNA of the microorganism. Multiple copies of the gene which encodes mannose PTS can be introduced into the chromosomal DNA of the microorganism by homologous recombination, using a target sequence which is present in multiple copies on the chromosomal DNA. Examples of sequences which are present in multiple copies include repetitive DNA and inverted repeats present on the ends of transposable elements. Also, these genes may be ligated in tandem with the manXYZ operon on the chromosome or incorporated by duplication on unnecessary genes on the chromosome. These genes can be introduced using a temperature-sensitive vector or integration vector. With the manX, manY, and manZ genes forming an operon structure (hereafter, referred to as "manXYZ operon"), it is more effective to increase the copy number of the manXYZ operon.

As disclosed in JP2-109985A, the gene encoding mannose PTS can be incorporated into a transposon, and the transposon transferred to incorporate multiple copies into the chromosomal DNA. The presence of the gene on the chromosome can be confirmed by Southern hybridization using a part of the gene encoding mannose PTS as a probe.

Aside from increasing the copy number of the gene described above, expression of the gene encoding the mannose PTS can also be enhanced by employing the methods described in WO00/18935, such as by substituting the expression regulatory sequence of the manXYZ operon promoter, etc., on the chromosomal DNA or plasmid with a stronger one, approximating the −35, −10 regions to the consensus sequence, amplifying a regulator which can enhance the expression of the manXYZ operon, and deleting or weakening a regulator which would decrease the expression of the manXYZ operon. For example, the lac promoter, trp promoter, trc promoter, tac promoter, araBA promoter, lambda phage PR promoter, PL promoter, tet promoter, T7 promoter, φ10 promoter, etc., are all known as strong promoters. It is also possible to introduce a base substitution, etc., into the manXYZ operon's promoter region and SD region to achieve greater promoter strength.

Examples of methods for evaluating the strength of promoters and examples of strong promoters are described in articles by Goldstein et al. (Prokaryotic promoters in biotechnology. Biotechnol. Annu. Rev., 1995, 1, 105-128), etc. Furthermore, substituting several nucleotides in the spacer region between a ribosome binding site (RBS) and a start codon, particularly into the sequence immediately upstream of a start codon, is known to have a strong effect on mRNA translation efficiency. These can be modified. The expression regulatory regions of the manXYZ operon's promoter, etc., can be determined by promoter search vectors and gene analysis software such as GENETYX, etc. Expression of the gene encoding the mannose PTS can be strengthened by substitutions or modifications of these promoters. Substitution of expression regulatory sequences can be conducted, for example, employing temperature-sensitive plasmids or the Red-driven integration method (WO2005/010175).

In order to increase the activity of the mannose PTS protein, a mutation which increases the activity of mannose PTS may also be introduced to the manX, Y, Z genes. Examples of mutations which increase the activity of the protein encoded by the manX, Y, Z genes includes a mutation of the promoter sequence, which increases the transcription amount of the manXYZ operon, and a mutation within the encoded region of the gene, which increases the specific activity of the mannose PTS.

<2> Method for Producing L-amino Acid

The method for producing L-amino acid of the present invention includes culturing the microorganism of the present invention in a medium, allowing the L-amino acid to accumulate in the medium or in the microorganism, and collecting the L-amino acid from the medium or microorganism.

Mediums conventionally used in the fermentation of microorganisms to produce L-amino acids may be used in the present invention. That is, an ordinary medium containing a carbon source, nitrogen source, non-organic ions, and other organic components as needed may be used. Carbon sources include a sugar, such as glucose, sucrose, lactose, galactose, fructose, a starch hydrolysase, etc.; an alcohol, such as glycerol, solbitol, etc.; an organic acid, such as fumaric acid, citric acid, succinic acid, etc. Of these, it is preferable to use glucose as the carbon source. Nitrogen sources include an inorganic ammonium salt, such as ammonium sulfate, ammonium chloride, ammonium phosphate, etc., an organic nitrogen, such as a soybean hydrolysis product, etc., ammonia gas, ammonia water, etc. It is desirable for the organic micronutrient sources to contain the appropriate amount of the auxotrophic substances, such as vitamin B1, L-homoserine, etc., or yeast extract, etc. In addition to these, according to necessity, small amounts of potassium phosphate, magnesium sulfate, iron ions, manganese ions, etc., can be added.

The medium may be either a natural or synthetic medium as long as it contains a carbon source, nitrogen source, inorganic ions, and, as needed, other organic micronutrients.

It is recommended that the culture be performed under aerobic conditions for 1-7 days at a culture temperature of 24° C.-37° C., with a pH during the culture of 5-9. To adjust the pH, an inorganic or organic acidic or alkali substance, and ammonia gas, and the like, may be used. L-amino acid can be collected from the fermentation solution using a combination of a conventional methods, such as ion-exchange resin, precipitation, and other known methods.

If the L-amino acid accumulates inside the cells of the microorganism, the cells can be crushed by ultrasound, etc., then removed by centrifugal separation to obtain the supernatant, from which the L-amino acid can be collected using an ion-exchange resin method, etc.

It is also possible to use a liquid medium appropriate for production of L-glutamic acid by precipitation, and to perform the culture while the L-glutamic acid is produced and collects in the medium. Conditions for production of L-glutamic acid include, for example, a pH of 5.0-4.0, preferably a pH of 4.5-4.0, more preferably a pH of 4.3-4.0, and even more preferably a pH of 4.0.

Any known recovery method may be used for collecting the L-glutamic acid from the culture solution after completion of the culture. For example, L-glutamic acid can be collected by concentration crystallization after removing the cells from the culture solution, or via ion-exchange chromatography, etc. When culturing under L-glutamic acid producing conditions, the L-glutamic acid which precipitates in the culture solution can also be collected via centrifugal separation, filtering, etc. In this case, the L-glutamic acid dissolved in the culture may be crystallized and then isolated.

Furthermore, an animal feed additive using the produced fermentation broth can be prepared by using a separation method. L-amino acid separation methods such as centrifuging, filtering, decanting, flocculating, or a combination of these can be used to remove or reduce biomass.

The obtained broth can be concentrated using known methods such as a rotary evaporator, thin layer evaporator, reverse osmosis, or nanofiltration (FR8613346B, U.S. Pat. No. 4,997,754, EP410005B, JP1073646B).

The concentrated broth is then processed using the methods of freeze-drying, spray-drying, spray granulation, or any other process to give a preferably free flowing, finely divided powder. This can then be used as an animal feed additive. This free-flowing finely divided powder can be converted into a coarse-grain, very free flowing, stable and largely dust-free product by using suitable compacting or granulating processes. Altogether, more than 90% of the water is removed in this way so that the water concentration of the animal feed additive is less than 10%, preferably less than 5% by weight.

The protein content of the feed additive can be less than 10%, preferably less than 5% by weight, and the concentration of L-threonine can be more than 50%, preferably more than 85%, more preferably more than 95% (U.S. Pat. No. 5,431,933, JP1214636B, U.S. Pat. Nos. 4,956,471, 4,777,051, 4,946,654, 5,840,358, 6,238,714, US2005/0025878).

The separation steps described above do not necessarily have to be performed, but may be combined in a technically expedient manner.

EXAMPLES

The following more specifically describes the present invention, by way of the following non-limiting examples.

Reference Examples

Reference Example 1

Construction of an L-lysine-producing Bacterium

<1-1> Construction of a Strain with Disrupted cadA and ldcC Genes which Encode Lysine Decarboxylase First, a strain which does not produce lysine decarboxylase was constructed. The Red-driven integration method described in WO WO2005/010175 and a λ phage excision system (J. Bacteriol. 2002 September; 184 (18): 5200-3. Interactions between integrase and excisionase in the phage lambda excisive nucleoprotein complex. Cho E H, Gumport R I, Gardner J F) were used to construct a strain with disrupted lysine decarboxylase genes.

Lysine decarboxylase is encoded by the cadA gene (Genbank Accession No. NP_418555. SEQ ID No. 42) and the ldcC gene (Genbank Accession No. NP_414728. SEQ ID No. 44) (WO96/17930). The WC196 strain was used as the parent strain. WC196 strain was named *Escherichia coli* AJ13069, and deposited on Dec. 6, 1994 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14690 and converted to an international deposit under the Budapest Treaty on Sep. 29, 1995, and given Accession No. FERM BP-5252.

The cadA and ldcC genes encoding lysine decarboxylase were deleted using a method called "Red-driven integration," which was initially developed by Datsenko and Wanner (Proc. Natl. Acad. Sci. USA, 2000, vol. 97, No. 12, pp. 6640-6645), and a λ phage excision system (J. Bacteriol. 2002 September; 184 (18): 5200-3). According to the "Red-driven integration" method, it is possible to construct a gene-disrupted strain in a single step by using a PCR product obtained with a synthetic oligonucleotide primer derived from the 5' terminal end of the target gene and the 3'terminal end of the antibiotic-resistant gene. Furthermore, via λ phage excision, the antibiotic-resistant gene, which is integrated into chromosome, can be removed from the strain.

(1) Disruption of the cadA Gene

The pMW118-attL-Cm-attR plasmid described below was used as the PCR template. pMW118-attL-Cm-attR was obtained by inserting the attL and attR-attachment site of α-phage and the cat gene, which is an antibiotic-resistant gene, into pMW118 (Takara Bio Inc.), in the order of attL-cat-attR (see WO2005/010175). The attL sequence is shown in SEQ ID No. 11, and the attR sequence is shown in SEQ ID No. 12.

PCR was conducted using as primers the synthetic oligonucleotides shown in SEQ ID Nos. 46 and 47, wherein a sequence corresponding to both ends of attL and attR was at the primer's 3' end and a sequence corresponding to part of the cadA gene, the target gene, was at the primer's 5' end.

The amplified PCR product was purified with an agarose gel, then introduced by electroporation into an *Escherichia coli* WC196 strain containing plasmid pKD46, which has a temperature-sensitive replication origin. Plasmid pKD46 (Proc. Natl. Acad. Sci. USA, 2000, vol. 97, No. 12, pp. 6640-6645) includes the λ phage DNA fragment (2154 bases), and includes the genes (γ, β, and exo) that encode Red recombinase in the λ Red homologous recombination system under the control of the arabinose-induced ParaB promoter (GenBank/EMBL Accession No. J02459, 31088th-33241st).

Competent cells for electroporation were prepared as follows. The *Escherichia coli* WC196 strain was cultured overnight at 30° C. in LB medium containing 100 mg/L ampicillin, and then was diluted 100 times in 5 mL SOB medium containing ampicillin (20 mg/L) and L-arabinose (1 mM) (Molecular Cloning: Lab Manual 2nd edition, Sambrook, J., et al., Cold Spring Harbor Laboratory Press (1989)). The dilution product was cultured at 30° C. until OD 600 to approx. 0.6, and then was concentrated 100 fold and washed three times with 10% glycerol in preparation for electroporation.

Electroporation was performed using 70 μl competent cells and approx. 100 ng PCR product. 1 mL SOC medium (Molecular Cloning: Lab Manual 2nd edition, Sambrook, J., et al., Cold Spring Harbor Laboratory Press (1989)) was added and cultured at 37° C. for 2.5 hours, then cultured on a plate medium of L-agar containing Cm (chloramphenicol) (25 mg/L) at 37° C. and the Cm-resistant recombinants were selected. Next, to remove the pKD46 plasmid, cells were subcultured twice on an L-agar medium containing Cm at 42° C. The ampicillin resistance of the colony was tested, and an ampicillin-sensitive strain without pKD46 was obtained.

Deletion of the cadA gene in the mutant identified by the chloramphenicol-resistant gene was confirmed using PCR. The cadA deficient strain was designated WC196AcadA::att-cat.

Next, to remove the att-cat gene which is introduced into the cadA gene, a helper plasmid, pMW-intxis-ts, described below, was used. pMW-intxis-contains a gene (SEQ ID No. 13) that encodes λ phage integrase (Int) and a gene (SEQ ID No. 15) that encodes excisionase (Xis) and has a temperature-sensitive replication origin. By introducing pMW-intxis-ts, attL (SEQ ID No. 11) and attR (SEQ ID No. 12) on the chromosome are recognized, causing recombination, and the genes between attL and attR are excised, leaving only the attL or attR sequence on the chromosome.

Competent cells of the WC196AcadA::att-cat strain obtained as described above were prepared using a typical method, and were transformed with the helper plasmid pMW-intxis-ts, cultured on a plate medium of L-agar containing 50 mg/L ampicillin at 30° C., thus selecting the ampicillin-resistant strain. Next, to remove the pMW-intxis-ts plasmid, the transformants were subcultured on an L-agar medium at 42° C., the ampicillin resistance and the chloramphenicol resistance of the colony obtained were tested, and a chloramphenicol- and ampicillin-sensitive strain from which the att-cat and pMW-intxis-ts were removed was obtained. This strain was designated WC196ΔcadA.

(2) Deletion of the ldcC Gene in the WC196ΔcadA Strain

The ldcC gene in the WC196ΔcadA strain was deleted in accordance with the technique described above, using primers having the sequences of SEQ ID Nos. 48 and 49 as the ldcC disrupting primers. This results in WC196ΔcadAΔldcC, in which both cadA and ldcC are disrupted.

(3) Preparation of the PCR Template and Helper Plasmid

The PCR template pMW118-attL-Cm-attR and helper plasmid pMW-intxis-ts were prepared as follows.

(3-1) pMW118-attL-Cm-attR pMW118-attL-Tc-attR was constructed based on pMW118-attL-Cm-attR. The following four DNA fragments were prepared:

1) BglII-EcoRI DNA fragment (120 bp) (SEQ ID No. 11) containing attL obtained by PCR amplification of the sequence corresponding to the chromosome of the *E. coli* W3350 strain (ATCC31278 containing λ prophage), using oligonucleotides P1 and P2 (SEQ ID Nos. 17 & 18) as primers (these primers additionally contained the recognition sites of the BglII and EcoRI endonucleases), 2) PstI-HindIII DNA fragment (182 bp) (SEQ ID No. 12) containing attR obtained by PCR amplification of the sequence corresponding to the chromosome of the E. coli W3350 strain (containing λ prophage), using oligonucleotides P3 and P4 (SEQ ID Nos. 19 & 20) as primers (these primers additionally contained the recognition sites of the PstI and HindIII endonucleases), 3) BglII-HindIII large fragment (3916 bp) of pMW118-ter_rrnB:The pMW118-ter_rrnB was obtained by ligating the following three fragments:

i) A large fragment (2359 bp) containing an AatII-EcoRI-pol fragment from pMW118 obtained by digesting the pMW118 with an EcoRI restriction endonuclease, treating it with a Klenow fragment of DNA polymerase I, then digesting the fragment with an AatII restriction endonuclease, ii) An AatII-BglII small fragment (1194 bp) of pUC19 containing the ampicillin-resistant (ApR) bla gene obtained by PCR-amplifying the sequence corresponding to the pUC19 plasmid, using oligonucleotides P5 and P6 (SEQ ID Nos. 21 & 22) as primers (these primers additionally contained the recognition sites of the AatII and BglII endonucleases), iii) A small BglII-PstIpol fragment (363 bp) containing transcription terminator ter_rrnB obtained by PCR-amplifying the region corresponding to the chromosome of the E. coli MG1655 strain, using oligonucleotides P7 and P8 (SEQ ID Nos. 23 & 24) as primers (these primers additionally contained the recognition sites of the BglII and PstI endonucleases), 4) A small EcoRI-PstI fragment (1388 bp) (SEQ ID No. 29) of pML-Tc-ter_thrL containing a tetracycline-resistant gene and transcription terminator ter_thrL. The pML-Tc-ter_thrL was obtained as follows.

A pML-MSC (Mol Biol (Mosk). 2005 September-October; 39(5):823-31; Biotechnologiya (Russian) No. 5: 3-20)) was digested with XbaI and BamHI restriction endonucleases, and a large fragment of this (3342 bp) was ligated with an XbaI-BamHI fragment (68 bp) that contained the terminator ter_thrL. The XbaI-BamHI fragment (68 bp) corresponded to the chromosome of E. coli MG1655, and was obtained by PCR amplification, using oligonucleotides P9 and P10 (SEQ ID Nos. 25 & 26) as primers (these primers additionally contained the recognition sites of the XbaI and BamHI endonucleases). The ligated reaction product was designated plasmid pML-ter_thrL.

The pML-ter_thrL was digested with KpnI and XbaI restriction endonucleases, treated with a Klenow fragment of DNA polymerase I, then ligated with a small EcoRI-Van91I fragment (1317 bp) of pBR322 containing the tetracycline-resistant gene (the pBR322 which was digested with EcoRI and Van91I restriction endonucleases was treated with a Klenow fragment of DNA polymerase I). The product of this ligation was designated plasmid pML-Tc-ter_thrL.

Next, the pMW118-attL-Cm-attR was constructed by ligation of a large BamHI-XbaI fragment (4413 bp), a PA2 promoter (initial promoter of T7 phage), a chloramphenicol-resistant (CmR) cat gene, an artificial BglII-XbaI DNA fragment (1162 bp) containing transcription terminator ter_thrL, and attR. The artificial DNA fragment (SEQ ID No. 30) was obtained as follows.

pML-MSC (Mol Biol (Mosk). 2005 September-October; 39(5):823-31; Biotechnologiya (Russian) No. 5: 3-20).) was digested with KpnI and XbaI restriction endonucleases, and ligated with a small KpnI-XbaI fragment (120 bp) containing a PA2 promoter (early promoter of T7 phage). A KpnI-XbaI fragment was obtained by amplifying the region corresponding to T7 phage DNA, using oligonucleotides P11 and P12 (SEQ ID Nos. 27 & 28) as primers (these primers additionally contained the recognition sites of the KpnI and XbaI endonucleases) by PCR. The product of the ligation was designated plasmid pML-PA2-MCS.

The XbaI site was removed from pML-PA2-MCS. The product was designated plasmid pML-PA2-MCS (XbaI-).

A small BglII-HindIII fragment (928 bp) of pML-PA2-MCS(XbaI-) containing a PA2 promoter (initial promoter of T7 phage) and chloramphenicol-resistant (CmR) cat gene was ligated with a small HindIII-HindIII fragment (234 bp) of pMW 118-attL-Tc-attR, which contained the transcription terminator ter_thrL, and attR.

The target artificial DNA fragment (1156 bp) was obtained by PCR amplification of the ligation mixture, using oligonucleotides P9 and P4 (SEQ ID Nos. 25 & 20) as primers (these primers contained the recognition sites of the HindIII and XbaI endonucleases).

(3-2) pMW-intxis-ts

First, two DNA fragments were amplified based on λ phage DNA (Fermentas) as the template. The first fragment contained nt 37168-38046 of the genome of λ phage DNA (SEQ ID No. 39), and contained a cI repressor, Prm and Pr promoters, and the leader sequence of the cro gene. This fragment was obtained by amplification, using oligonucleotides P1' and P2' (SEQ ID Nos. 31 & 32) as primers. The second fragment contained nt 27801-29100 of the genome of λ phage DNA (SEQ ID No. 40), which contained the xis-int gene from λ phage DNA. This fragment was obtained by PCR, using oligonucleotides P3' and P4' (SEQ ID Nos. 33 & 34) as primers. All of the primers contained the proper endonuclease recognition sites.

The first PCR-amplified fragment, which contained the cI repressor, was digested with the ClaI restriction endonuclease, and then digested with the EcoRI restriction endonuclease.

The second PCR fragment was digested with EcoRI and PstI endonucleases. The plasmid pMWPlaclacI-ts was digested with BglII endonuclease, treated with the Klenow fragment of DNA polymerase I, and then digested with the PstI restriction endonuclease. A vector fragment of pMWPlaclacI-ts was eluted from an agarose gel and ligated with the cut PCR-amplified fragment.

The plasmid pMWPlaclacI-ts is a derivative of pMWPlaclacI containing the following parts: 1) an artificial BglII-HindIII DNA fragment containing a PlacUV5 promoter and the lacI gene under control of the RBS of the bacteriophage T7 gene 10; 2) an AatII-BglII fragment containing the ampicillin-resistant (ApR) gene obtained by PCR amplification of the region corresponding to the pUC19 plasmid, using oligonucleotides P5' and P6' (SEQ ID Nos. 35 & 36) as primers (these primers contained the recognition sites of the AatII and BglII endonucleases); 3) an AatII-HindIII fragment containing an AatII-PvuI fragment of a recombinant plasmid pMW118-ter_rrnB.

The plasmid pMW118-ter_rrnB was constructed as follows. A PstI-HindIII fragment containing a terminator ter_rrnB was obtained by PCR amplification of the region corresponding to the chromosome of the E. coli MG1655 strain, using as primers oligonucleotides P7' and P8' (SEQ ID Nos. 37 & 38) which contained proper endonuclease recognition sites. Prior to ligation, the pMW118 and ter_rrnB fragments (complementary strand of SEQ ID No. 41) were digested with PvuI or PstI, respectively, treated with the Klenow fragment of DNA polymerase I to blunt the ends, and then digested with AatII or HindIII endonuclease. In the construction of the pMWPlaclacI-ts mutant, an AatII-EcoRV fragment of plasmid pMWPlaclacI was substituted with an AatII-EcoRV fragment of plasmid pMAN997 which contained the par, ori, and repAts genes of the pSC101 replicon. (Applied and Environmental Microbiology, June 2005, p. 3228-32)

Example 1

Construction of the Plasmid Used to Increase Mannose PTS Activity

<1-1> Construction of the Plasmid for manXYZ Overexpression

The entire genome sequence of the *Escherichia coli* chromosome (*Escherichia coli* K-12 strain) has been determined (Science, 277, 1453-1474 (1997)). Based on the nucleotide sequences of the manXYZ genes (Genbank Accession Nos. NP416331, 416332, 416333), using as a 5' primer the synthetic oligonucleotide of SEQ ID No. 5 having an Sse8387I site, and as a 3' primer the synthetic oligonucleotide of SEQ ID No. 6 having an XbaI site, PCR was performed using the chromosomal DNA of the *Escherichia Coli* MG1655 strain as the template, and a gene fragment that contained the manXYZ genes was obtained.

The purified PCR product was ligated with vector pMW219, which had been digested with Sse8387I (Takara Shuzo) and XbaI (Nippon Gene Co., Ltd.) to construct a plasmid pM-manXYZ for manXYZ overexpression. This plasmid was under the control of a lac promoter, and the manXYZ genes were replaced downstream of the lac promoter. pM-manXYZ was digested with Sse8387I and EcoRI, the manXYZ gene fragments were collected and purified, and ligated to vector pSTV29 which had been digested with Sse8387I and EcoRI (Takara Shuzo). In this way, the plasmid pS-manXYZ for overexpression was constructed.

<1-2> Construction of Plasmid for ptsG Overexpression

In the same manner as with the above-mentioned manXYZ genes, a plasmid for expressing the ptsG (SEQ ID No. 50) gene was constructed. Using as a 5' primer the synthetic oligonucleotide of SEQ ID No. 7 containing a HindIII site, and as a 3' primer the synthetic oligonucleotide of SEQ ID No. 8 containing an XbaI site, PCR was performed with the chromosomal DNA of the *Escherichia Coli* MG1655 strain as the template, and this was treated with restriction endonucleases HindIII and XbaI, thus a gene fragment which contained ptsG was obtained. The purified PCR product was ligated with vector pMW219, which had been digested with HindIII and XbaI, to construct plasmid pM-ptsG for amplifying ptsG. This plasmid was under the control of a lac promoter, and the ptsG gene was placed downstream from the lac promoter. In the same manner as with the manXYZ, the ptsG gene fragment was excised from the pM-ptsG, and ligated to vector pSTV29, and the plasmid pS-ptsG for ptsG overexpression was constructed.

Example 2

Construction of the Strain Exhibiting manXYZ Gene Overexpression and Evaluation of L-Lysine Production by the Strain As an *Escherichia coli* L-lysine-producing strain, the WC196ΔldcCΔcadA (pCABD2) strain was used as the parent strain, and the lys-producing plasmid pCABD2 carrying the dapA, dapB, and lysC genes (WO01/53459) was introduced into the WC196ΔldcCΔcadA strain in Reference Example 1.

The WC196ΔldcCΔcadA (pCABD2) strain was transformed with the manXYZ-amplifying plasmid pM-manXYZ and the ptsG-amplifying plasmid pM-ptsG constructed in Example 1, as well as the control plasmid pMW219, and kanamycin-resistant strains were obtained. After confirming that the desired plasmids had been introduced, the strain with the manXYZ-overexpression plasmid pM-manXYZ was designated WC196ΔldcCΔcadA (pCABD2, pM-manXYZ); the strain with the ptsG-overexpression plasmid pM-ptsG was designated WC196ΔldcCΔcadA (pCABD2, pM-ptsG); and the strain with control plasmid pMW219 was designated WC196ΔldcCΔcadA (pCABD2, pMW219).

The strains constructed as above were cultured in L medium containing 25 mg/L kanamycin at 37° C. until OD600=0.6. After that, an equal amount of a 40% glycerol solution was added to the culture and stirred, then appropriate amounts were pipetted and stored at −80° C. This was called the glycerol stock.

After melting the glycerol stocks of these strains, 100 μL of each was evenly spread onto an L plate containing 25 mg/L kanamycin, and this was cultured at 37° C. for 24 hours. Approx. ⅛ of the cells on the plate were inoculated into a 20 mL fermentation medium with 25 mg/L kanamycin contained in a 500 mL Sakaguchi shaking flask, and cultured at 37° C. for 24 hours using a reciprocating shaking culture apparatus. After culturing, the amount of L-lysine which had accumulated in the medium was measured using a Biotech-analyzer AS210 (Sakura Seiki).

The OD and L-lysine present at the 24th hour are shown in Table 2. As shown in Table 2, a large amount of L-lysine accumulated in the WC196ΔldcCΔcadA (pCABD2, pM-manXYZ) strain, compared to the WC196ΔldcCΔcadA (pCABD2, pMW219) strain without the manXYZ genes. An improvement in the amount of produced lysine was also confirmed compared to the WC196ΔldcCΔcadA (pCABD2, pM-ptsG) strain without the ptsG gene. Such data showed that overexpression of the manXYZ genes is more effective in L-lysine production than overexpression of the ptsG.

TABLE 2

| Strain | OD600 | Lys-HCl (g/L) |
|---|---|---|
| WC196ΔldcCΔcadA (pCABD2, pMW219) | 12.6 | 10.0 |
| WC196ΔldcCΔcadA (pCABD2, pM-manXYZ) | 16.3 | 16.4 |
| WC196ΔldcCΔcadA (pCABD2, pM-ptsG) | 15.8 | 14.7 |

Culture period: 24 hours

Medium for L-lysine-production:

| | |
|---|---|
| Glucose | 40 g/L |
| Ammonium sulfate | 24 g/L |
| Potassium Dihydrogen Phosphate | 1.0 g/L |
| Magnesium sulfate 7-hydrate | 1.0 g/L |
| Ferrous sulfate 4•7-hydrate | 0.01 g/L |
| Manganese sulfate 4•7-hydrate | 0.01 g/L |
| Yeast extract | 2.0 g/L |
| Calcium carbonate | 30 g/L |

Adjusted to pH 7.0 with KOH, sterilized at 115° C. for 10 min.

Glucose and MgSO$_4$.7H$_2$O were sterilized separately.

Example 3

Effect of manXYZ Overexpression on an L-glutamic Acid-producing Strain of Bacteria of the Genus *Escherichia*

The AJ12949 strain was used as an *Escherichia coli* L-glutamic acid-producing parent strain. The AJ12949 strain has reduced α-ketoglutarate dehydrogenase activity, and was deposited on Dec. 28, 1993 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14039 and converted to an international deposit under the Budapest Treaty on Nov. 11, 1994, and given Accession No. FERM BP-4881.

The AJ12949 strain was transformed with the manXYZ overexpression plasmid pS-manXYZ constructed in Example 1, and the control plasmid pSTV29, thus obtaining chloramphenicol-resistant strains. After confirming that the desired plasmids had been introduced, the strain with the manXYZ overexpression plasmid pS-manXYZ was designated AJ12949 (pS-manXYZ); and the with the control plasmid pSTV29 was designated AJ12949 (pSTV29).

The AJ12949 (pS-manXYZ) strain and the AJ12949 (pSTV29) strain were cultured in L medium containing 20 mg/L chloramphenicol at 37° C. until reaching OD600=0.6. After this, an equal amount of a 40% glycerol solution was added to the culture and stirred, and then appropriate amounts were pipetted to obtain a glycerol stock and stored at −80° C.

After melting the glycerol stocks of these strains, 100 μL of each was evenly spread onto an L plate containing 20 mg/L chloramphenicol, and this was cultured at 3° C. for 24 hours. Approx. ⅛ of the cells on the plate obtained were inoculated into a 20 mL fermentation medium described below with 20 mg/L chloramphenicol contained in a 500 mL Sakaguchi shaking flask, and cultured at 37° C. for 40 hours using a reciprocating shaking culture apparatus. After culturing, the amount of L-glutamic acid which had accumulated in the medium was measured using a Biotech-analyzer AS210 (Sakura Seiki).

The OD and L-glutamic acid which had accumulated at the 40th hour are shown in Table 3. As shown in Table 3, a large amount of L-glutamic acid had accumulated in the AJ12949 (pS-manXYZ) strain, compared to the AJ12949 (pSTV29) strain which had not been transformed with the manXYZ genes.

TABLE 3

| Bacterial strain | OD600 | L-Glu (g/L) |
|---|---|---|
| AJ12949 (pSTV29) | 14.7 | 18.6 |
| AJ12949 (pS-manXYZ) | 16.6 | 20.0 |

Culture period: 40 hours

Medium for L-Glutamic Acid Production:

| Glucose | 40 g/L |
|---|---|
| Ammonium sulfate | 20 g/L |
| Potassium Dihydrogen Phosphate | 1.0 g/L |

-continued

| Magnesium sulfate 7-hydrate | 1.0 g/L |
|---|---|
| Ferrous sulfate 4•7-hydrate | 0.01 g/L |
| Manganese sulfate 4•7-hydrate | 0.01 g/L |
| Yeast extract | 2.0 g/L |
| Calcium carbonate | 30 g/L |

Adjusted to pH 7.0 with KOH, sterilized at 115° C. for 10 min.

Glucose and MgSO$_4$.7H$_2$O were sterilized separately. Also, after the culture temperature came down to 60° C. or lower, a thiamine hydrochloride solution which had been sterilized with a DISMIC-25cs 0.2 mm filter (ADVANTEC) was added to obtain the final concentration of 0.01 g/L.

Example 4

Effect of Mannose PTS Overexpression on an L-threonine-producing Strain of Bacteria of the Genus *Escherichia*

The B-5318 strain can be used as the parent strain for L-threonine-production resulting from manXYZ overexpression. The B-5318 strain was deposited on May 3, 1990 with the Russian National Collection of Industrial Microorganisms (VKPM), GNII Genetika (Russia, 117545 Moscow, 1 Dorozhny Proezd, 1) under Accession No. VKPM B-5318. The construction of the strains overexpressing manXYZ from B-5318 can be performed using the plasmid described in Example 1.

The B-5318 strain was transformed with the manXYZ-overexpression plasmid pS-manXYZ used in Example 1 and the control plasmid pSTV29, and chloramphenicol-resistant strains were obtained. After confirming that the desired plasmids had been introduced, the strain containing the manXYZ-overexpression plasmid pS-manXYZ was designated B-5318 (pS-manXYZ); and the strain containing the control plasmid pSTV29 was designated B-5318 (pSTV29).

The B-5318 (pS-manXYZ) strain and the B-5318 (pSTV29) strain were cultured in an L medium containing 20 mg/L chloramphenicol at 37° C. until OD600=0.6. After this, an equal volume of 40% glycerol solution was added to the culture and stirred, and then appropriate amounts were pipetted to obtain a glycerol stock and stored at −80° C.

After melting the glycerol stock of these strains, 100 μL of each was evenly spread onto an L plate containing 20 mg/L chloramphenicol, and this was cultured at 37° C. for 24 hours. Approx. ⅛ of the cells on the plate were inoculated into 20 mL fermentation medium with 20 mg/L chloramphenicol in a 500 mL Sakaguchi shaking flask, and cultured at 37° C. for 40 hours using a reciprocating shaking culture apparatus. After culturing, the amount of L-threonine which had accumulated in the medium was measured using high-performance liquid chromatography.

The OD and L-threonine present at the 40th hour are shown in Table 4. As shown in the table, a large amount of L-threonine had accumulated in the B-5318 (pS-manXYZ) strain, compared to the B-5318 (pSTV29) strain which had not been transformed with the manXYZ gene.

TABLE 4

| Bacterial strain | OD600 | L-threonine (g/L) |
|---|---|---|
| B-5318 (pSTV29) | 11.7 | 6.1 |
| B-5318 (pS-manXYZ) | 15.6 | 7.4 |

Medium for L-threonine-production:

| | |
|---|---|
| Glucose | 60 g/L |
| Ammonium sulfate | 16 g/L |
| Potassium Dihydrogen Phosphate | 0.7 g/L |
| Magnesium sulfate 7-hydrate | 1.0 g/L |
| Ferrous sulfate 7-hydrate | 0.01 g/L |
| Manganese sulfate 7-hydrate | 0.01 g/L |
| Yeast extract | 0.5 g/L |
| Thiamine hydrochloride | 0.2 mg/L |
| L-isoleucine | 0.05 g/L |
| Calcium carbonate | 30 g/L |

Adjusted to pH 7.0 with KOH, sterilized at 115° C. for 10 min.

Glucose and $MgSO_4 \cdot 7H_2O$ were sterilized separately. Potassium hydroxide was sterilized by dry heat at 180° C. for 3 hours. After the culture temperature came down to 60° C. or lower, a thiamine hydrochloride solution which had been sterilized with a DISMIC-25cs 0.2 mm filter (ADVANTEC) was added to obtain the final concentration of 0.2 mg/L.

Example 5

Effect of Mannose PTS Enhancement on an L-Glutamic Acid-Producing Strain of Bacteria of the Genus *Pantoea*

The *Pantoea ananatis* AJ13601 strain can be used as the parent strain for L-threonine-production resulting from mannose PTS amplification. The *Pantoea ananatis* AJ13601 strain was deposited on Aug. 18, 1999 with the National Institute of Bioscience and Human Technology, Agency of Industrial Science and Technology, Ministry of Economy, Trade and Industry (1-3, Higashi 1-chome, Tsukuba-shi, Ibaraki-ken 305-8566) under Accession No. FERM P-17516 and converted to an international deposit under the Budapest Treaty on Jul. 6, 2000, and given Accession No. FERM BP-7207. The manXYZ overexpressed strains can be constructed from L-glutamic acid-producing bacteria using the plasmid described in example 1.

The mannose PTS overexpressed strains are cultured in an L-glutamic acid-production medium and then cultured using a reciprocating shaking culture apparatus. After culturing, the amount of L-glutamic acid which accumulates in the medium is measured using Biotech analyzer AS210 (Sakura Seiki). The mannose PTS overexpressed strain with improved L-glutamic acid-producing ability can be obtained.

While the invention has been described in detail with reference to preferred embodiments thereof, it will be apparent to one skilled in the art that various changed can be made, and equivalents employed, without departing from the scope of the invention. All documents cited herein are hereby incorporated by reference.

The invention claimed is:

1. A method for producing an L-amino acid comprising:
  A) culturing in a medium an *E.coli* microorganism which has the ability to produce an L-amino acid and which has been modified to enhance mannose PTS activity as compared to a non-modified microorganism, and
  B) collecting the L-amino acid from the medium or the microorganism; wherein said mannose PTS activity is enhanced by increasing expression of an *E.coli* manXYZ gene by a method selected from the group consisting of:
  i) increasing the copy number of the gene,
  ii) modifying the expression regulatory sequence of the gene, and
  iii) combinations thereof.

2. The method according to claim 1, wherein the manXYZ gene encodes a protein selected from the group consisting of:
  (A) a protein comprising an amino acid sequence selected from the group consisting of SEQ ID Nos. 2, 3, 4, and combinations thereof,
  (B) a protein comprising an amino acid sequence selected from the group consisting of SEQ ID Nos. 2, 3, and 4, wherein said amino acid sequence includes 1 to 20 substitutions, deletions, insertions, additions, or inversions of amino acid residues, and has mannose PTS activity.

3. The method according to claim 1, wherein the manXYZ gene is a DNA selected from the group consisting of:
  (a) a DNA comprising the nucleotide sequence of nucleotides 72 to 2767 in SEQ ID No. 1,
  (b) a DNA encoding a protein having mannose PTS activity which hybridizes with:
    i) a sequence complementary to the nucleotide sequence of 72 to 2767 in SEQ ID No. 1, or
    ii) a probe prepared from said nucleotide sequence under stringent conditions comprising washing at 60° C. in 1×SSC, 0.1% SDS.

4. The method according to claim 1, wherein said L-amino acid is selected from the group consisting of L-lysine, L-threonine, L-glutamic acid, and combinations thereof.

5. The method according to claim 2, wherein said manXYZ gene encodes a protein selected from the group consisting of:
  A) a protein comprising the amino acid sequences of SEQ ID NOs: 2, 3, and 4; and p1 B) a protein comprising the amino acid sequences of SEQ ID NOs: 2, 3, and 4, wherein said amino acid sequence includes 1 to 20 substitutions, deletions, insertions, additions, or inversions of amino acid residues and has mannose PTS activity.

6. The method according to claim 5, wherein said manXYZ gene encodes a protein comprising the amino acid sequences of SEQ ID NOs: 2, 3, and 4.

\* \* \* \* \*

SEQUENCE LISTING

```
<160> NUMBER OF SEQ ID NOS: 51

<210> SEQ ID NO 1
<211> LENGTH: 2770
<212> TYPE: DNA
<213> ORGANISM: Escherichia coli
<220> FEATURE:
<221> NAME/KEY: CDS
<222> LOCATION: (72)..(1043)
<220> FEATURE:
<221> NAME/KEY: CDS
<222> LOCATION: (1106)..(1906)
<220> FEATURE:
<221> NAME/KEY: CDS
<222> LOCATION: (1910)..(2770)

<400> SEQUENCE: 1
tcgattgtgg acgacgattc aaaaatacat ctggcacgtt gaggtgttaa cgataataaa         60
ggaggtagca a gtg acc att gct att gtt ata ggc aca cat ggt tgg gct        110
            Val Thr Ile Ala Ile Val Ile Gly Thr His Gly Trp Ala
              1               5                  10 gca gag cag ttg ctt aaa acg gca gaa atg ctg tta ggc gag cag gaa        158
Ala Glu Gln Leu Leu Lys Thr Ala Glu Met Leu Leu Gly Glu Gln Glu
    15                  20                  25 aac gtc ggc tgg atc gat ttc gtt cca ggt gaa aat gcc gaa acg ctg        206
Asn Val Gly Trp Ile Asp Phe Val Pro Gly Glu Asn Ala Glu Thr Leu
30                  35                  40                  45 att gaa aag tac aac gct cag ttg gca aaa ctc gac acc act aaa ggc        254
Ile Glu Lys Tyr Asn Ala Gln Leu Ala Lys Leu Asp Thr Thr Lys Gly
                50                  55                  60 gtg ctg ttt ctc gtt gat aca tgg gga ggc agc ccg ttc aat gct gcc        302
Val Leu Phe Leu Val Asp Thr Trp Gly Gly Ser Pro Phe Asn Ala Ala
            65                  70                  75
```

-continued

| | |
|---|---|
| agc cgc att gtc gtc gac aaa gag cat tat gaa gtc att gca ggc gtt<br>Ser Arg Ile Val Val Asp Lys Glu His Tyr Glu Val Ile Ala Gly Val<br>       80                    85                    90 | 350 |
| aac att cca atg ctc gtg gaa acg tta atg gcc cgt gat gat gac cca<br>Asn Ile Pro Met Leu Val Glu Thr Leu Met Ala Arg Asp Asp Asp Pro<br>95                      100                    105 | 398 |
| agc ttt gat gaa ctg gtg gca ctg gca gta gaa aca ggc cgt gaa ggc<br>Ser Phe Asp Glu Leu Val Ala Leu Ala Val Glu Thr Gly Arg Glu Gly<br>110                 115                 120              125 | 446 |
| gtg aaa gca ctg aaa gcc aaa ccg gtt gaa aaa gcc gcg cca gca ccc<br>Val Lys Ala Leu Lys Ala Lys Pro Val Glu Lys Ala Ala Pro Ala Pro<br>               130                 135                 140 | 494 |
| gct gcc gca gca cca aaa gcg gct cca act ccg gca aaa cca atg ggg<br>Ala Ala Ala Ala Pro Lys Ala Ala Pro Thr Pro Ala Lys Pro Met Gly<br>                145                 150                155 | 542 |
| cca aac gac tac atg gtt att ggc ctt gcg cgt atc gac gac cgt ctg<br>Pro Asn Asp Tyr Met Val Ile Gly Leu Ala Arg Ile Asp Asp Arg Leu<br>             160                 165                170 | 590 |
| att cac ggt cag gtc gcc acc cgc tgg acc aaa gaa acc aat gtc tcc<br>Ile His Gly Gln Val Ala Thr Arg Trp Thr Lys Glu Thr Asn Val Ser<br>175                    180                    185 | 638 |
| cgt att att gtt gtt agt gat gaa gtg gct gcg gat acc gtt cgt aag<br>Arg Ile Ile Val Val Ser Asp Glu Val Ala Ala Asp Thr Val Arg Lys<br>190                      195                    200                205 | 686 |
| aca ctg ctc acc cag gtt gca cct ccg ggc gta aca gca cac gta gtt<br>Thr Leu Leu Thr Gln Val Ala Pro Pro Gly Val Thr Ala His Val Val<br>                       210                 215                220 | 734 |
| gat gtt gcc aaa atg att cgc gtc tac aac aac ccg aaa tat gct ggc<br>Asp Val Ala Lys Met Ile Arg Val Tyr Asn Asn Pro Lys Tyr Ala Gly<br>               225                 230                235 | 782 |
| gaa cgc gta atg ctg tta ttt acc aac cca aca gat gta gag cgt ctc<br>Glu Arg Val Met Leu Leu Phe Thr Asn Pro Thr Asp Val Glu Arg Leu<br>             240                 245                250 | 830 |
| gtt gaa ggc ggc gtg aaa atc acc tct gtt aac gtc ggt ggt atg gca<br>Val Glu Gly Gly Val Lys Ile Thr Ser Val Asn Val Gly Gly Met Ala<br>255                    260                    265 | 878 |
| ttc cgt cag ggt aaa acc cag gtg aat aac gcg gtt tcg gtt gat gaa<br>Phe Arg Gln Gly Lys Thr Gln Val Asn Asn Ala Val Ser Val Asp Glu<br>270                      275                    280                285 | 926 |
| aaa gat atc gag gcg ttc aag aaa ctg aat gcg cgc ggt att gag ctg<br>Lys Asp Ile Glu Ala Phe Lys Lys Leu Asn Ala Arg Gly Ile Glu Leu<br>               290                 295                300 | 974 |
| gaa gtc cgt aag gtt tcc acc gat ccg aaa ctg aaa atg atg gat ctg<br>Glu Val Arg Lys Val Ser Thr Asp Pro Lys Leu Lys Met Met Asp Leu<br>                       305                 310                315 | 1022 |
| atc agc aaa atc gat aag taa cgtattgtgt tgattatcac tcagttttca<br>Ile Ser Lys Ile Asp Lys<br>             320 | 1073 |
| cacttaagtc ttacgtaaac aggagaagta ca atg gag att acc act ctt caa<br>                                                    Met Glu Ile Thr Thr Leu Gln<br>                                                       325                    330 | 1126 |
| att gtg ctg gta ttt atc gta gcc tgt atc gca ggt atg gga tca atc<br>Ile Val Leu Val Phe Ile Val Ala Cys Ile Ala Gly Met Gly Ser Ile<br>                           335                      340                    345 | 1174 |
| ctc gat gaa ttt cag ttt cac cgt ccg cta atc gcg tgt acc ctg gtg<br>Leu Asp Glu Phe Gln Phe His Arg Pro Leu Ile Ala Cys Thr Leu Val<br>                       350                    355                360 | 1222 |
| ggt atc gtt ctt ggg gat atg aaa acc ggt att att atc ggt ggt acg<br>Gly Ile Val Leu Gly Asp Met Lys Thr Gly Ile Ile Ile Gly Gly Thr | 1270 |

-continued

```
                365                 370                 375
ctg gaa atg atc gcg ctg ggc tgg atg aac atc ggt gct gca gtt gcg      1318
Leu Glu Met Ile Ala Leu Gly Trp Met Asn Ile Gly Ala Ala Val Ala
        380                 385                 390 cct gac gcc gct ctg gct tct atc att tct acc att ctg gtt atc gca      1366
Pro Asp Ala Ala Leu Ala Ser Ile Ile Ser Thr Ile Leu Val Ile Ala
395                 400                 405                 410 ggt cat cag agc att ggt gca ggt atc gca ctg gca atc cct ctg gcc      1414
Gly His Gln Ser Ile Gly Ala Gly Ile Ala Leu Ala Ile Pro Leu Ala
                415                 420                 425 gct gcg ggc cag gta ctg acc atc atc gtt cgt act att acc gtt gct      1462
Ala Ala Gly Gln Val Leu Thr Ile Ile Val Arg Thr Ile Thr Val Ala
        430                 435                 440 ttc cag cac gct gcg gat aag gct gct gat aac ggc aac ctg aca gcg      1510
Phe Gln His Ala Ala Asp Lys Ala Ala Asp Asn Gly Asn Leu Thr Ala
                445                 450                 455 att tcc tgg atc cac gtt tct tct ctg ttc ctg caa gca atg cgt gtg      1558
Ile Ser Trp Ile His Val Ser Ser Leu Phe Leu Gln Ala Met Arg Val
460                 465                 470 gct att ccg gcc gtc atc gtt gcg ctg tct gtt ggt acc agc gaa gta      1606
Ala Ile Pro Ala Val Ile Val Ala Leu Ser Val Gly Thr Ser Glu Val
475                 480                 485                 490 cag aac atg ctg aat gcg att ccg gaa gtg gtg acc aat ggt ctg aat      1654
Gln Asn Met Leu Asn Ala Ile Pro Glu Val Val Thr Asn Gly Leu Asn
                495                 500                 505 atc gcc ggt ggc atg atc gtg gtg gtt ggt tat gcg atg gtt atc aac      1702
Ile Ala Gly Gly Met Ile Val Val Val Gly Tyr Ala Met Val Ile Asn
        510                 515                 520 atg atg cgt gct ggc tac ctg atg ccg ttc ttc tac ctc ggc ttc gta      1750
Met Met Arg Ala Gly Tyr Leu Met Pro Phe Phe Tyr Leu Gly Phe Val
        525                 530                 535 acc gca gca ttc acc aac ttt aac ctg gtt gct ctg ggt gtg att ggt      1798
Thr Ala Ala Phe Thr Asn Phe Asn Leu Val Ala Leu Gly Val Ile Gly
540                 545                 550 act gtt atg gca gtg ctc tac atc caa ctt agc ccg aaa tac aac cgc      1846
Thr Val Met Ala Val Leu Tyr Ile Gln Leu Ser Pro Lys Tyr Asn Arg
555                 560                 565                 570 gta gcc ggt gcg cct gct cag gca gct ggt aac aac gat ctc gat aac      1894
Val Ala Gly Ala Pro Ala Gln Ala Ala Gly Asn Asn Asp Leu Asp Asn
                575                 580                 585 gaa ctg gac taa cag gtg agc gaa atg gtt gat aca act caa act acc      1942
Glu Leu Asp     Val Ser Glu Met Val Asp Thr Thr Gln Thr Thr
                590                 595                 600 acc gag aaa aaa ctc act caa agt gat att cgt ggc gtc ttc ctg cgt      1990
Thr Glu Lys Lys Leu Thr Gln Ser Asp Ile Arg Gly Val Phe Leu Arg
                605                 610                 615 tct aac ctc ttc cag ggt tca tgg aac ttc gaa cgt atg cag gca ctg      2038
Ser Asn Leu Phe Gln Gly Ser Trp Asn Phe Glu Arg Met Gln Ala Leu
            620                 625                 630 ggt ttc tgc ttc tct atg gta ccg gca att cgt cgc ctc tac cct gag      2086
Gly Phe Cys Phe Ser Met Val Pro Ala Ile Arg Arg Leu Tyr Pro Glu
            635                 640                 645 aac aac gaa gct cgt aaa caa gct att cgc cgt cac ctg gag ttc ttt      2134
Asn Asn Glu Ala Arg Lys Gln Ala Ile Arg Arg His Leu Glu Phe Phe
650                 655                 660 aac acc cag ccg ttc gtg gct gcg ccg att ctc ggc gta acc ctg gcg      2182
Asn Thr Gln Pro Phe Val Ala Ala Pro Ile Leu Gly Val Thr Leu Ala
665                 670                 675                 680 ctg gaa gaa cag cgt gct aat ggc gca gag atc gac gac ggt gct atc      2230
Leu Glu Glu Gln Arg Ala Asn Gly Ala Glu Ile Asp Asp Gly Ala Ile
```

-continued

```
Leu Glu Glu Gln Arg Ala Asn Gly Ala Glu Ile Asp Asp Gly Ala Ile
                685                 690                 695 aac ggt atc aaa gtc ggt ttg atg ggg cca ctg gct ggt gta ggc gac    2278
Asn Gly Ile Lys Val Gly Leu Met Gly Pro Leu Ala Gly Val Gly Asp
            700                 705                 710 ccg atc ttc tgg gga acc gta cgt ccg gta ttt gca gca ctg ggt gcc    2326
Pro Ile Phe Trp Gly Thr Val Arg Pro Val Phe Ala Ala Leu Gly Ala
            715                 720                 725 ggt atc gcg atg agc ggc agc ctg tta ggt ccg ctg ctg ttc ttc atc    2374
Gly Ile Ala Met Ser Gly Ser Leu Leu Gly Pro Leu Leu Phe Phe Ile
            730                 735                 740 ctg ttt aac ctg gtg cgt ctg gca acc cgt tac tac ggc gta gcg tat    2422
Leu Phe Asn Leu Val Arg Leu Ala Thr Arg Tyr Tyr Gly Val Ala Tyr
745                 750                 755                 760 ggt tac tcc aaa ggt atc gat atc gtt aaa gat atg ggt ggt ggc ttc    2470
Gly Tyr Ser Lys Gly Ile Asp Ile Val Lys Asp Met Gly Gly Gly Phe
                765                 770                 775 ctg caa aaa ctg acg gaa ggg gcg tct atc ctc ggc ctg ttt gtc atg    2518
Leu Gln Lys Leu Thr Glu Gly Ala Ser Ile Leu Gly Leu Phe Val Met
                780                 785                 790 ggg gca ttg gtt aac aag tgg aca cat gtc aac atc ccg ctg gtt gtc    2566
Gly Ala Leu Val Asn Lys Trp Thr His Val Asn Ile Pro Leu Val Val
                795                 800                 805 tct cgc att act gac cag acg ggc aaa gaa cac gtt act act gtc cag    2614
Ser Arg Ile Thr Asp Gln Thr Gly Lys Glu His Val Thr Thr Val Gln
810                 815                 820 act att ctg gac cag tta atg cca ggc ctg gta cca ctg ctg ctg acc    2662
Thr Ile Leu Asp Gln Leu Met Pro Gly Leu Val Pro Leu Leu Leu Thr
825                 830                 835                 840 ttt gct tgt atg tgg cta ctg cgc aaa aaa gtt aac ccg ctg tgg atc    2710
Phe Ala Cys Met Trp Leu Leu Arg Lys Lys Val Asn Pro Leu Trp Ile
                845                 850                 855 atc gtt ggc ttc ttc gtc atc ggt atc gct ggt tac gct tgc ggc ctg    2758
Ile Val Gly Phe Phe Val Ile Gly Ile Ala Gly Tyr Ala Cys Gly Leu
                860                 865                 870 ctg gga ctg taa                                                    2770
Leu Gly Leu
        875

<210> SEQ ID NO 2
<211> LENGTH: 323
<212> TYPE: PRT
<213> ORGANISM: Escherichia coli

<400> SEQUENCE: 2

Val Thr Ile Ala Ile Val Ile Gly Thr His Gly Trp Ala Ala Glu Gln
1               5                   10                  15

Leu Leu Lys Thr Ala Glu Met Leu Leu Gly Glu Gln Glu Asn Val Gly
            20                  25                  30

Trp Ile Asp Phe Val Pro Gly Glu Asn Ala Glu Thr Leu Ile Glu Lys
        35                  40                  45

Tyr Asn Ala Gln Leu Ala Lys Leu Asp Thr Thr Lys Gly Val Leu Phe
    50                  55                  60

Leu Val Asp Thr Trp Gly Gly Ser Pro Phe Asn Ala Ala Ser Arg Ile
65                  70                  75                  80

Val Val Asp Lys Glu His Tyr Glu Val Ile Ala Gly Val Asn Ile Pro
                85                  90                  95

Met Leu Val Glu Thr Leu Met Ala Arg Asp Asp Pro Ser Phe Asp
            100                 105                 110
```

```
Glu Leu Val Ala Leu Ala Val Glu Thr Gly Arg Glu Gly Val Lys Ala
            115                 120                 125

Leu Lys Ala Lys Pro Val Glu Lys Ala Ala Pro Ala Pro Ala Ala Ala
        130                 135                 140

Ala Pro Lys Ala Ala Pro Thr Pro Ala Lys Pro Met Gly Pro Asn Asp
145                 150                 155                 160

Tyr Met Val Ile Gly Leu Ala Arg Ile Asp Asp Arg Leu Ile His Gly
                165                 170                 175

Gln Val Ala Thr Arg Trp Thr Lys Glu Thr Asn Val Ser Arg Ile Ile
            180                 185                 190

Val Val Ser Asp Glu Val Ala Ala Asp Thr Val Arg Lys Thr Leu Leu
        195                 200                 205

Thr Gln Val Ala Pro Pro Gly Val Thr Ala His Val Val Asp Val Ala
    210                 215                 220

Lys Met Ile Arg Val Tyr Asn Asn Pro Lys Tyr Ala Gly Glu Arg Val
225                 230                 235                 240

Met Leu Leu Phe Thr Asn Pro Thr Asp Val Glu Arg Leu Val Glu Gly
                245                 250                 255

Gly Val Lys Ile Thr Ser Val Asn Val Gly Gly Met Ala Phe Arg Gln
            260                 265                 270

Gly Lys Thr Gln Val Asn Asn Ala Val Ser Val Asp Glu Lys Asp Ile
        275                 280                 285

Glu Ala Phe Lys Lys Leu Asn Ala Arg Gly Ile Glu Leu Glu Val Arg
    290                 295                 300

Lys Val Ser Thr Asp Pro Lys Leu Lys Met Met Asp Leu Ile Ser Lys
305                 310                 315                 320

Ile Asp Lys

<210> SEQ ID NO 3
<211> LENGTH: 266
<212> TYPE: PRT
<213> ORGANISM: Escherichia coli

<400> SEQUENCE: 3

Met Glu Ile Thr Thr Leu Gln Ile Val Leu Val Phe Ile Val Ala Cys
1               5                   10                  15

Ile Ala Gly Met Gly Ser Ile Leu Asp Glu Phe Gln Phe His Arg Pro
            20                  25                  30

Leu Ile Ala Cys Thr Leu Val Gly Ile Val Leu Gly Asp Met Lys Thr
        35                  40                  45

Gly Ile Ile Ile Gly Gly Thr Leu Glu Met Ile Ala Leu Gly Trp Met
    50                  55                  60

Asn Ile Gly Ala Ala Val Ala Pro Asp Ala Ala Leu Ala Ser Ile Ile
65                  70                  75                  80

Ser Thr Ile Leu Val Ile Ala Gly His Gln Ser Ile Gly Ala Gly Ile
                85                  90                  95

Ala Leu Ala Ile Pro Leu Ala Ala Ala Gly Gln Val Leu Thr Ile Ile
            100                 105                 110

Val Arg Thr Ile Thr Val Ala Phe Gln His Ala Ala Asp Lys Ala Ala
        115                 120                 125

Asp Asn Gly Asn Leu Thr Ala Ile Ser Trp Ile His Val Ser Ser Leu
    130                 135                 140

Phe Leu Gln Ala Met Arg Val Ala Ile Pro Ala Val Ile Val Ala Leu
145                 150                 155                 160
```

```
Ser Val Gly Thr Ser Glu Val Gln Asn Met Leu Asn Ala Ile Pro Glu
                165                 170                 175

Val Val Thr Asn Gly Leu Asn Ile Ala Gly Gly Met Ile Val Val Val
            180                 185                 190

Gly Tyr Ala Met Val Ile Asn Met Met Arg Ala Gly Tyr Leu Met Pro
        195                 200                 205

Phe Phe Tyr Leu Gly Phe Val Thr Ala Ala Phe Thr Asn Phe Asn Leu
    210                 215                 220

Val Ala Leu Gly Val Ile Gly Thr Val Met Ala Val Leu Tyr Ile Gln
225                 230                 235                 240

Leu Ser Pro Lys Tyr Asn Arg Val Ala Gly Ala Pro Ala Gln Ala Ala
                245                 250                 255

Gly Asn Asn Asp Leu Asp Asn Glu Leu Asp
                260                 265

<210> SEQ ID NO 4
<211> LENGTH: 286
<212> TYPE: PRT
<213> ORGANISM: Escherichia coli

<400> SEQUENCE: 4

Val Ser Glu Met Val Asp Thr Thr Gln Thr Thr Thr Glu Lys Lys Leu
1               5                   10                  15

Thr Gln Ser Asp Ile Arg Gly Val Phe Leu Arg Ser Asn Leu Phe Gln
            20                  25                  30

Gly Ser Trp Asn Phe Glu Arg Met Gln Ala Leu Gly Phe Cys Phe Ser
        35                  40                  45

Met Val Pro Ala Ile Arg Arg Leu Tyr Pro Glu Asn Asn Glu Ala Arg
    50                  55                  60

Lys Gln Ala Ile Arg Arg His Leu Glu Phe Phe Asn Thr Gln Pro Phe
65                  70                  75                  80

Val Ala Ala Pro Ile Leu Gly Val Thr Leu Ala Leu Glu Glu Gln Arg
                85                  90                  95

Ala Asn Gly Ala Glu Ile Asp Asp Gly Ala Ile Asn Gly Ile Lys Val
            100                 105                 110

Gly Leu Met Gly Pro Leu Ala Gly Val Gly Asp Pro Ile Phe Trp Gly
        115                 120                 125

Thr Val Arg Pro Val Phe Ala Ala Leu Gly Ala Gly Ile Ala Met Ser
    130                 135                 140

Gly Ser Leu Leu Gly Pro Leu Leu Phe Phe Ile Leu Phe Asn Leu Val
145                 150                 155                 160

Arg Leu Ala Thr Arg Tyr Tyr Gly Val Ala Tyr Gly Tyr Ser Lys Gly
                165                 170                 175

Ile Asp Ile Val Lys Asp Met Gly Gly Gly Phe Leu Gln Lys Leu Thr
            180                 185                 190

Glu Gly Ala Ser Ile Leu Gly Leu Phe Val Met Gly Ala Leu Val Asn
        195                 200                 205

Lys Trp Thr His Val Asn Ile Pro Leu Val Val Ser Arg Ile Thr Asp
    210                 215                 220

Gln Thr Gly Lys Glu His Val Thr Thr Val Gln Thr Ile Leu Asp Gln
225                 230                 235                 240

Leu Met Pro Gly Leu Val Pro Leu Leu Leu Thr Phe Ala Cys Met Trp
                245                 250                 255

Leu Leu Arg Lys Lys Val Asn Pro Leu Trp Ile Ile Val Gly Phe Phe
```

```
                  260                 265                 270
Val Ile Gly Ile Ala Gly Tyr Ala Cys Gly Leu Leu Gly Leu
            275                 280                 285
```

<210> SEQ ID NO 5
<211> LENGTH: 34
<212> TYPE: DNA
<213> ORGANISM: Artificial
<220> FEATURE:
<223> OTHER INFORMATION: Synthesized

<400> SEQUENCE: 5
acacaccctg caggaaagga ggtagcaagt gacc         34

<210> SEQ ID NO 6
<211> LENGTH: 30
<212> TYPE: DNA
<213> ORGANISM: Artificial
<220> FEATURE:
<223> OTHER INFORMATION: Synthesized

<400> SEQUENCE: 6
tgtgtctaga aaaggaattg ccagcagggt              30

<210> SEQ ID NO 7
<211> LENGTH: 31
<212> TYPE: DNA
<213> ORGANISM: Artificial
<220> FEATURE:
<223> OTHER INFORMATION: Synthesized

<400> SEQUENCE: 7
cacaaaagct tcatactcag gagcactctc a            31

<210> SEQ ID NO 8
<211> LENGTH: 31
<212> TYPE: DNA
<213> ORGANISM: Artificial
<220> FEATURE:
<223> OTHER INFORMATION: Synthesized

<400> SEQUENCE: 8
gtgtgtctag aaactggcaa atcgcgtgt a             31

<210> SEQ ID NO 9
<211> LENGTH: 101
<212> TYPE: DNA
<213> ORGANISM: lambda phage

<400> SEQUENCE: 9
cctgcttttt tatactaagt tggcattata aaaaagcatt gcttatcaat tgttgcaac      60 gaacaggtca ctatcagtca aaataaaatc attatttgat t                        101

<210> SEQ ID NO 10
<211> LENGTH: 172
<212> TYPE: DNA
<213> ORGANISM: lambda phage

<400> SEQUENCE: 10
gcgctaatgc tctgttacag gtcactaata ccatctaagt agttgattca tagtgactgc    60
atatgttgtg ttttacagta ttatgtagtc tgttttttat gcaaaatcta atttaatata    120
ttgatattta tcattttta cgtttctcgt tcagctttt tatactaact tg              172

<210> SEQ ID NO 11
<211> LENGTH: 120
<212> TYPE: DNA
<213> ORGANISM: lambda phage

<400> SEQUENCE: 11

```
agatcttgaa gcctgctttt ttatactaag ttggcattat aaaaaagcat tgcttatcaa    60
tttgttgcaa cgaacaggtc actatcagtc aaaataaaat cattatttga tttcgaattc   120
```

<210> SEQ ID NO 12
<211> LENGTH: 184
<212> TYPE: DNA
<213> ORGANISM: lambda phage

<400> SEQUENCE: 12

```
ctgcagtctg ttacaggtca ctaataccat ctaagtagtt gattcatagt gactgcatat    60
gttgtgtttt acagtattat gtagtctgtt tttatgcaa atctaattt aatatattga    120
tatttatatc attttacgtt tctcgttcag cttttttata ctaacttgag cgtctagaaa   180
gctt                                                                184
```

<210> SEQ ID NO 13
<211> LENGTH: 1071
<212> TYPE: DNA
<213> ORGANISM: lambda phage
<220> FEATURE:
<221> NAME/KEY: CDS
<222> LOCATION: (1)..(1071)

<400> SEQUENCE: 13

```
atg gga aga agg cga agt cat gag cgc cgg gat tta ccc cct aac ctt     48
Met Gly Arg Arg Arg Ser His Glu Arg Arg Asp Leu Pro Pro Asn Leu
1               5                  10                  15 tat ata aga aac aat gga tat tac tgc tac agg gac cca agg acg ggt     96
Tyr Ile Arg Asn Asn Gly Tyr Tyr Cys Tyr Arg Asp Pro Arg Thr Gly
                20                  25                  30 aaa gag ttt gga tta ggc aga gac agg cga atc gca atc act gaa gct    144
Lys Glu Phe Gly Leu Gly Arg Asp Arg Arg Ile Ala Ile Thr Glu Ala
            35                  40                  45 ata cag gcc aac att gag tta ttt tca gga cac aaa cac aag cct ctg    192
Ile Gln Ala Asn Ile Glu Leu Phe Ser Gly His Lys His Lys Pro Leu
        50                  55                  60 aca gcg aga atc aac agt gat aat tcc gtt acg tta cat tca tgg ctt    240
Thr Ala Arg Ile Asn Ser Asp Asn Ser Val Thr Leu His Ser Trp Leu
65                  70                  75                  80 gat cgc tac gaa aaa atc ctg gcc agc aga gga atc aag cag aag aca    288
Asp Arg Tyr Glu Lys Ile Leu Ala Ser Arg Gly Ile Lys Gln Lys Thr
                85                  90                  95 ctc ata aat tac atg agc aaa att aaa gca ata agg agg ggt ctg cct    336
Leu Ile Asn Tyr Met Ser Lys Ile Lys Ala Ile Arg Arg Gly Leu Pro
            100                 105                 110 gat gct cca ctt gaa gac atc acc aca aaa gaa att gcg gca atg ctc    384
Asp Ala Pro Leu Glu Asp Ile Thr Thr Lys Glu Ile Ala Ala Met Leu
        115                 120                 125 aat gga tac ata gac gag ggc aag gcg gcg tca gcc aag tta atc aga    432
Asn Gly Tyr Ile Asp Glu Gly Lys Ala Ala Ser Ala Lys Leu Ile Arg
    130                 135                 140 tca aca ctg agc gat gca ttc cga gag gca ata gct gaa ggc cat ata    480
Ser Thr Leu Ser Asp Ala Phe Arg Glu Ala Ile Ala Glu Gly His Ile
145                 150                 155                 160
```

| | | | | | | | | | | | | | | | | |
|---|---|---|---|---|---|---|---|---|---|---|---|---|---|---|---|---|
| aca | aca | aac | cat | gtc | gct | gcc | act | cgc | gca | gca | aaa | tca | gag | gta | agg | 528 |
| Thr | Thr | Asn | His | Val | Ala | Ala | Thr | Arg | Ala | Ala | Lys | Ser | Glu | Val | Arg | |
| | | | | 165 | | | | | 170 | | | | | 175 | | |
| aga | tca | aga | ctt | acg | gct | gac | gaa | tac | ctg | aaa | att | tat | caa | gca | gca | 576 |
| Arg | Ser | Arg | Leu | Thr | Ala | Asp | Glu | Tyr | Leu | Lys | Ile | Tyr | Gln | Ala | Ala | |
| | | 180 | | | | | 185 | | | | | 190 | | | | |
| gaa | tca | tca | cca | tgt | tgg | ctc | aga | ctt | gca | atg | gaa | ctg | gct | gtt | gtt | 624 |
| Glu | Ser | Ser | Pro | Cys | Trp | Leu | Arg | Leu | Ala | Met | Glu | Leu | Ala | Val | Val | |
| | 195 | | | | | 200 | | | | | 205 | | | | | |
| acc | ggg | caa | cga | gtt | ggt | gat | tta | tgc | gaa | atg | aag | tgg | tct | gat | atc | 672 |
| Thr | Gly | Gln | Arg | Val | Gly | Asp | Leu | Cys | Glu | Met | Lys | Trp | Ser | Asp | Ile | |
| 210 | | | | | 215 | | | | | 220 | | | | | | |
| gta | gat | gga | tat | ctt | tat | gtc | gag | caa | agc | aaa | aca | ggc | gta | aaa | att | 720 |
| Val | Asp | Gly | Tyr | Leu | Tyr | Val | Glu | Gln | Ser | Lys | Thr | Gly | Val | Lys | Ile | |
| 225 | | | | | 230 | | | | | 235 | | | | | 240 | |
| gcc | atc | cca | aca | gca | ttg | cat | att | gat | gct | ctc | gga | ata | tca | atg | aag | 768 |
| Ala | Ile | Pro | Thr | Ala | Leu | His | Ile | Asp | Ala | Leu | Gly | Ile | Ser | Met | Lys | |
| | | | | 245 | | | | | 250 | | | | | 255 | | |
| gaa | aca | ctt | gat | aaa | tgc | aaa | gag | att | ctt | ggc | gga | gaa | acc | ata | att | 816 |
| Glu | Thr | Leu | Asp | Lys | Cys | Lys | Glu | Ile | Leu | Gly | Gly | Glu | Thr | Ile | Ile | |
| | | 260 | | | | | 265 | | | | | 270 | | | | |
| gca | tct | act | cgt | cgc | gaa | ccg | ctt | tca | tcc | ggc | aca | gta | tca | agg | tat | 864 |
| Ala | Ser | Thr | Arg | Arg | Glu | Pro | Leu | Ser | Ser | Gly | Thr | Val | Ser | Arg | Tyr | |
| | 275 | | | | | 280 | | | | | 285 | | | | | |
| ttt | atg | cgc | gca | cga | aaa | gca | tca | ggt | ctt | tcc | ttc | gaa | ggg | gat | ccg | 912 |
| Phe | Met | Arg | Ala | Arg | Lys | Ala | Ser | Gly | Leu | Ser | Phe | Glu | Gly | Asp | Pro | |
| 290 | | | | | 295 | | | | | 300 | | | | | | |
| cct | acc | ttt | cac | gag | ttg | cgc | agt | ttg | tct | gca | aga | ctc | tat | gag | aag | 960 |
| Pro | Thr | Phe | His | Glu | Leu | Arg | Ser | Leu | Ser | Ala | Arg | Leu | Tyr | Glu | Lys | |
| 305 | | | | | 310 | | | | | 315 | | | | | 320 | |
| cag | ata | agc | gat | aag | ttt | gct | caa | cat | ctt | ctc | ggg | cat | aag | tcg | gac | 1008 |
| Gln | Ile | Ser | Asp | Lys | Phe | Ala | Gln | His | Leu | Leu | Gly | His | Lys | Ser | Asp | |
| | | | | 325 | | | | | 330 | | | | | 335 | | |
| acc | atg | gca | tca | cag | tat | cgt | gat | gac | aga | ggc | agg | gag | tgg | gac | aaa | 1056 |
| Thr | Met | Ala | Ser | Gln | Tyr | Arg | Asp | Asp | Arg | Gly | Arg | Glu | Trp | Asp | Lys | |
| | | | 340 | | | | | 345 | | | | | 350 | | | |
| att | gaa | atc | aaa | taa | | | | | | | | | | | | 1071 |
| Ile | Glu | Ile | Lys | | | | | | | | | | | | | |
| | | 355 | | | | | | | | | | | | | | |

<210> SEQ ID NO 14
<211> LENGTH: 356
<212> TYPE: PRT
<213> ORGANISM: lambda phage

<400> SEQUENCE: 14

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro

```
                100                 105                 110
Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355

<210> SEQ ID NO 15
<211> LENGTH: 219
<212> TYPE: DNA
<213> ORGANISM: lambda phage
<220> FEATURE:
<221> NAME/KEY: CDS
<222> LOCATION: (1)..(219)

<400> SEQUENCE: 15 atg tac ttg aca ctt cag gag tgg aac gca cgc cag cga cgt cca aga      48
Met Tyr Leu Thr Leu Gln Glu Trp Asn Ala Arg Gln Arg Arg Pro Arg
1               5                   10                  15 agc ctt gaa aca gtt cgt cga tgg gtt cgg gaa tgc agg ata ttc cca      96
Ser Leu Glu Thr Val Arg Arg Trp Val Arg Glu Cys Arg Ile Phe Pro
                20                  25                  30 cct ccg gtt aag gat gga aga gag tat ctg ttc cac gaa tca gcg gta     144
Pro Pro Val Lys Asp Gly Arg Glu Tyr Leu Phe His Glu Ser Ala Val
            35                  40                  45 aag gtt gac tta aat cga cca gta aca ggt ggc ctt ttg aag agg atc     192
Lys Val Asp Leu Asn Arg Pro Val Thr Gly Gly Leu Leu Lys Arg Ile
50                  55                  60 aga aat ggg aag aag gcg aag tca tga                                 219
Arg Asn Gly Lys Lys Ala Lys Ser
```

```
                                                        65                  70

<210> SEQ ID NO 16
<211> LENGTH: 72
<212> TYPE: PRT
<213> ORGANISM: lambda phage

<400> SEQUENCE: 16

Met Tyr Leu Thr Leu Gln Glu Trp Asn Ala Arg Gln Arg Arg Pro Arg
1               5                   10                  15

Ser Leu Glu Thr Val Arg Arg Trp Val Arg Glu Cys Arg Ile Phe Pro
            20                  25                  30

Pro Pro Val Lys Asp Gly Arg Glu Tyr Leu Phe His Glu Ser Ala Val
        35                  40                  45

Lys Val Asp Leu Asn Arg Pro Val Thr Gly Gly Leu Leu Lys Arg Ile
    50                  55                  60

Arg Asn Gly Lys Lys Ala Lys Ser
65                  70

<210> SEQ ID NO 17
<211> LENGTH: 40
<212> TYPE: DNA
<213> ORGANISM: Artificial Sequence
<220> FEATURE:
<223> OTHER INFORMATION: oligonucleotide P1

<400> SEQUENCE: 17
ctagtaagat cttgaagcct gctttttat actaagttgg                              40

<210> SEQ ID NO 18
<211> LENGTH: 41
<212> TYPE: DNA
<213> ORGANISM: Artificial Sequence
<220> FEATURE:
<223> OTHER INFORMATION: oligonucleotide P2

<400> SEQUENCE: 18
atgatcgaat tcgaaatcaa ataatgattt tattttgact g                           41

<210> SEQ ID NO 19
<211> LENGTH: 41
<212> TYPE: DNA
<213> ORGANISM: Artificial Sequence
<220> FEATURE:
<223> OTHER INFORMATION: oligonucleotide P3

<400> SEQUENCE: 19
atgccactgc agtctgttac aggtcactaa taccatctaa g                           41

<210> SEQ ID NO 20
<211> LENGTH: 46
<212> TYPE: DNA
<213> ORGANISM: Artificial Sequence
<220> FEATURE:
<223> OTHER INFORMATION: oligonucleotide P4

<400> SEQUENCE: 20
accgttaagc tttctagacg ctcaagttag tataaaaaag ctgaac                      46

<210> SEQ ID NO 21
<211> LENGTH: 38
<212> TYPE: DNA
<213> ORGANISM: Artificial Sequence
<220> FEATURE:
```

-continued

<223> OTHER INFORMATION: oligonucleotide P5

<400> SEQUENCE: 21
ttcttagacg tcaggtggca cttttcgggg aaatgtgc                           38

<210> SEQ ID NO 22
<211> LENGTH: 37
<212> TYPE: DNA
<213> ORGANISM: Artificial Sequence
<220> FEATURE:
<223> OTHER INFORMATION: oligonucleotide P6

<400> SEQUENCE: 22
taacagagat ctcgcgcaga aaaaaggat ctcaaga                             37

<210> SEQ ID NO 23
<211> LENGTH: 46
<212> TYPE: DNA
<213> ORGANISM: Artificial Sequence
<220> FEATURE:
<223> OTHER INFORMATION: oligonucleotide P7

<400> SEQUENCE: 23
aacagagatc taagcttaga tcctttgcct ggcggcagta gcgcgg                  46

<210> SEQ ID NO 24
<211> LENGTH: 35
<212> TYPE: DNA
<213> ORGANISM: Artificial Sequence
<220> FEATURE:
<223> OTHER INFORMATION: oligonucleotide P8

<400> SEQUENCE: 24
ataaactgca gcaaaaagag tttgtagaaa cgcaa                              35

<210> SEQ ID NO 25
<211> LENGTH: 36
<212> TYPE: DNA
<213> ORGANISM: Artificial Sequence
<220> FEATURE:
<223> OTHER INFORMATION: oligonucleotide P9

<400> SEQUENCE: 25
agtaattcta gaaagcttaa cacagaaaaa agcccg                             36

<210> SEQ ID NO 26
<211> LENGTH: 43
<212> TYPE: DNA
<213> ORGANISM: Artificial Sequence
<220> FEATURE:
<223> OTHER INFORMATION: oligonucleotide P10

<400> SEQUENCE: 26
ctagtaggat ccctgcagtg gtcgaaaaaa aaagcccgca ctg                     43

<210> SEQ ID NO 27
<211> LENGTH: 37
<212> TYPE: DNA
<213> ORGANISM: Artificial Sequence
<220> FEATURE:
<223> OTHER INFORMATION: oligonucleotide P11

<400> SEQUENCE: 27
atcgaggtac cagatctccg gataagtaga cagcctg                            37

<210> SEQ ID NO 28
<211> LENGTH: 32
<212> TYPE: DNA
<213> ORGANISM: Artificial Sequence
<220> FEATURE:
<223> OTHER INFORMATION: oligonucleotide P12

<400> SEQUENCE: 28
gaaggtctag agcgcccggt tgacgctgct ag                              32

<210> SEQ ID NO 29
<211> LENGTH: 1388
<212> TYPE: DNA
<213> ORGANISM: Artificial Sequence
<220> FEATURE:
<223> OTHER INFORMATION: cloned DNA fragment EcoRI-PstI including gene
      for tetracycline resistance (small EcoRI-Van91I fragment
      of pBR322) and transcription terminator ter_thrL

<400> SEQUENCE: 29
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
ccgccgccca gtcctgctcg cttcgctact tggagccact atcgactacg gatcatggc   360 gaccacaccc gtcctgtgga tcctctacgc cggacgcatc gtggccggca tcaccggcgc   420
cacaggtgcg gttgctggcg cctatatcgc cgacatcacc gatggggaag atcgggctcg   480
ccacttcggg ctcatgagcg cttgtttcgg cgtgggtatg gtggcaggcc ccgtggccgg   540
gggactgttg ggcgccatct ccttgcatgc accattcctt gcggcggcgg tgctcaacgg   600
cctcaaccta ctactgggct gcttcctaat gcaggagtcg cataagggag agcgtcgacc   660
gatgcccttg agagccttca acccagtcag ctccttccgg tgggcgcggg gcatgactat   720
cgtcgccgca cttatgactg tcttctttat catgcaactc gtaggacagg tgccggcagc   780
gctctgggtc attttcggcg aggaccgctt tcgctggagc gcgacgatga tcggcctgtc   840
gcttgcggta ttcggaatct tgcacgccct cgctcaagcc ttcgtcactg gtcccgccac   900
caaacgtttc ggcgagaagc aggccattat cgccggcatg gcggccgacg cgctgggcta   960
cgtcttgctg gcgttcgcga cgcgaggctg gatggccttc cccattatga ttcttctcgc  1020
ttccggcggc atcgggatgc ccgcgttgca ggccatgctg tccaggcagg tagatgacga  1080
ccatcaggga cagcttcaag gatcgctcgc ggctcttacc agcctaactt cgatcactgg  1140
accgctgatc gtcacggcga tttatgccgc ctcggcgagc acatggaacg ggttggcatg  1200
gattgtaggc gccgccctat accttgtctg cctccccgcg ttgcgtcgcg gtgcatggag  1260
ccgggccacc tcgacctgaa tggaagccgg cggcacctcg ctaacggatt caccactcca  1320
actagaaagc ttaacacaga aaaagcccg cacctgacag tgcgggcttt ttttttcgac  1380
cactgcag                                                         1388

<210> SEQ ID NO 30
<211> LENGTH: 1162
<212> TYPE: DNA
<213> ORGANISM: Artificial Sequence
<220> FEATURE:
<223> OTHER INFORMATION: cloned DNA fragment containing artificial DNA
      fragment including promoter PA2 (early promoter of phage T7), cat gene for chloramphenicol resistance (CmR),
transcription terminator ter_thrL and attR

<400> SEQUENCE: 30

```
agatctccgg ataagtagac agcctgataa gtcgcacgaa aaacaggtat tgacaacatg      60
aagtaacatg cagtaagata caaatcgcta ggtaacacta gcagcgtcaa ccgggcgctc     120
tagctagagc caagctagct tggccggatc cgagattttc aggagctaag gaagctaaaa     180
tggagaaaaa aatcactgga tataccaccg ttgatatatc ccaatggcat cgtaaagaac     240
attttgaggc atttcagtca gttgctcaat gtacctataa ccagaccgtt cagctggata     300
ttacggcctt tttaaagacc gtaaagaaaa ataagcacaa gttttatccg gcctttattc     360
acattcttgc ccgcctgatg aatgctcatc cggaattccg tatggcaatg aaagacggtg     420
agctggtgat atgggatagt gttcacccct gttacaccgt tttccatgag caaactgaaa     480
cgttttcatc gctctggagt gaataccacg acgatttccg gcagtttcta cacatatatt     540
cgcaagatgt ggcgtgttac ggtgaaaacc tggcctattt ccctaaaggg tttattgaga     600
atatgttttt cgtctcagcc aatccctggg tgagtttcac cagttttgat ttaaacgtgg     660
ccaatatgga caacttcttc gcccccgttt tcaccatggg caaatattat acgcaaggcg     720
acaaggtgct gatgccgctg gcgattcagg ttcatcatgc cgtctgtgat ggcttccatg     780
tcggcagaat gcttaatgaa ttacaacagt actgcgatga gtggcagggc ggggcgtaat     840
ttttttaagg cagttattgg tgcccttaaa cgcctggtgc tacgcctgaa taagtgataa     900
taagcggatg aatggcagaa attcgtcgaa gcttaacaca gaaaaaagcc cgcacctgac     960
agtgcgggct ttttttttcg accactgcag tctgttacag gtcactaata ccatctaagt    1020
agttgattca tagtgactgc atatgttgtg ttttacagta ttatgtagtc tgttttttat    1080
gcaaaatcta atttaatata ttgatattta tatcatttta cgtttctcgt tcagcttttt    1140
tatactaact tgagcgtcta ga                                             1162
```

<210> SEQ ID NO 31
<211> LENGTH: 27
<212> TYPE: DNA
<213> ORGANISM: Artificial Sequence
<220> FEATURE:
<223> OTHER INFORMATION: oligonucleotide P1'

<400> SEQUENCE: 31

```
ctaatatcga tgaagattct tgctcaa                                          27
```

<210> SEQ ID NO 32
<211> LENGTH: 34
<212> TYPE: DNA
<213> ORGANISM: Artificial Sequence
<220> FEATURE:
<223> OTHER INFORMATION: oligonucleotide P2'

<400> SEQUENCE: 32

```
gcgttgaatt ccatacaacc tccttagtac atgc                                  34
```

<210> SEQ ID NO 33
<211> LENGTH: 34
<212> TYPE: DNA
<213> ORGANISM: Artificial Sequence
<220> FEATURE:
<223> OTHER INFORMATION: oligonucleotide P3'

<400> SEQUENCE: 33

-continued gtactagaat tcgtgtaatt gcggagactt tgcg                                34

<210> SEQ ID NO 34
<211> LENGTH: 41
<212> TYPE: DNA
<213> ORGANISM: Artificial Sequence
<220> FEATURE:
<223> OTHER INFORMATION: oligonucleotide P4'

<400> SEQUENCE: 34
aatagcctgc agttatttga tttcaatttt gtcccactcc c                        41

<210> SEQ ID NO 35
<211> LENGTH: 38
<212> TYPE: DNA
<213> ORGANISM: Artificial Sequence
<220> FEATURE:
<223> OTHER INFORMATION: oligonucleotide P5'

<400> SEQUENCE: 35
ttcttagacg tcaggtggca cttttcgggg aaatgtgc                            38

<210> SEQ ID NO 36
<211> LENGTH: 37
<212> TYPE: DNA
<213> ORGANISM: Artificial Sequence
<220> FEATURE:
<223> OTHER INFORMATION: oligonucleotide P6'

<400> SEQUENCE: 36
taacagagat ctagcgcaga aaaaaggat ctcaaga                              37

<210> SEQ ID NO 37
<211> LENGTH: 35
<212> TYPE: DNA
<213> ORGANISM: Artificial Sequence
<220> FEATURE:
<223> OTHER INFORMATION: oligonucleotide P7'

<400> SEQUENCE: 37
ataaactgca gcaaaaagag tttgtagaaa cgcaa                               35

<210> SEQ ID NO 38
<211> LENGTH: 34
<212> TYPE: DNA
<213> ORGANISM: Artificial Sequence
<220> FEATURE:
<223> OTHER INFORMATION: oligonucleotide P8'

<400> SEQUENCE: 38
aacagaagct ttttgcctgg cggcagtagc gcgg                                34

<210> SEQ ID NO 39
<211> LENGTH: 879
<212> TYPE: DNA
<213> ORGANISM: Artificial Sequence
<220> FEATURE:
<223> OTHER INFORMATION: cloned DNA fragment containing cI repressor
     gene and promoter regions

<400> SEQUENCE: 39
tcgatgaaga ttcttgctca attgttatca gctatgcgcc gaccagaaca ccttgccgat    60
cagccaaacg tctcttcagg ccactgacta gcgataactt tccccacaac ggaacaactc   120
tcattgcatg ggatcattgg gtactgtggg tttagtggtt gtaaaaacac ctgaccgcta   180

```
tccctgatca gtttcttgaa ggtaaactca tcaccccccaa gtctggctat gcagaaatca      240
cctggctcaa cagcctgctc agggtcaacg agaattaaca ttccgtcagg aaagcttggc      300
ttggagcctg ttggtgcggt catggaatta ccttcaacct caagccagaa tgcagaatca      360 ctggctttt  tggttgtgct tacccatctc tccgcatcac ctttggtaaa ggttctaagc      420
tcaggtgaga acatccctgc ctgaacatga gaaaaaacag ggtactcata ctcacttcta      480
agtgacggct gcatactaac cgcttcatac atctcgtaga tttctctggc gattgaaggg      540
ctaaattctt caacgctaac tttgagaatt tttgcaagca atgcggcgtt ataagcattt      600
aatgcattga tgccattaaa taaagcacca acgcctgact gccccatccc catcttgtct      660
gcgacagatt cctgggataa gccaagttca ttttctttt  tttcataaat tgctttaagg      720
cgacgtgcgt cctcaagctg ctcttgtgtt aatggtttct tttttgtgct catacgttaa      780
atctatcacc gcaagggata aatatctaac accgtgcgtg ttgactattt tacctctggc      840
ggtgataatg gttgcatgta ctaaggaggt tgtatggaa                             879

<210> SEQ ID NO 40
<211> LENGTH: 1290
<212> TYPE: DNA
<213> ORGANISM: Artificial Sequence
<220> FEATURE:
<223> OTHER INFORMATION: cloned DNA fragment containing int-xis genes

<400> SEQUENCE: 40
attatttgat ttcaattttg tcccactccc tgcctctgtc atcacgatac tgtgatgcca       60
tggtgtccga cttatgcccg agaagatgtt gagcaaactt atcgcttatc tgcttctcat      120
agagtcttgc agacaaactg cgcaactcgt gaaaggtagg cggatcccct tcgaaggaaa      180
gacctgatgc ttttcgtgcg cgcataaaat accttgatac tgtgccggat gaaagcggtt      240
cgcgacgagt agatgcaatt atggtttctc cgccaagaat ctctttgcat ttatcaagtg      300
tttccttcat tgatattccg agagcatcaa tatgcaatgc tgttgggatg caatttta       360 cgcctgtttt gctttgctcg acataaagat atccatctac gatatcagac cacttcattt      420
cgcataaatc accaactcgt tgcccggtaa caacagccag ttccattgca agtctgagcc      480
aacatggtga tgattctgct gcttgataaa ttttcaggta ttcgtcagcc gtaagtcttg      540
atctccttac ctctgatttt gctgcgcgag tggcagcgac atggtttgtt gttatatggc      600
cttcagctat tgcctctcgg aatgcatcgc tcagtgttga tctgattaac ttggctgacg      660
ccgccttgcc ctcgtctatg tatccattga gcattgccgc aatttctttt gtggtgatgt      720
cttcaagtgg agcatcaggc agacccctcc ttattgcttt aattttgctc atgtaattta      780
tgagtgtctt ctgcttgatt cctctgctgg ccaggatttt ttcgtagcga tcaagccatg      840
aatgtaacgt aacggaatta tcactgttga ttctcgctgt cagaggcttg tgtttgtgtc      900
ctgaaaataa ctcaatgttg gcctgtatag cttcagtgat tgcgattcgc ctgtctctgc      960
ctaatccaaa ctctttaccc gtccttgggt ccctgtagca gtaatatcca ttgtttctta     1020
tataaaggtt aggggtaaa  tcccggcgct catgacttcg ccttcttccc atttctgatc     1080
ctcttcaaaa ggccacctgt tactggtcga tttaagtcaa cctttaccgc tgattcgtgg     1140
aacagatact ctcttccatc cttaaccgga ggtgggaata tcctgcattc ccgaacccat     1200
cgacgaactg tttcaaggct tcttggacgt cgctggcgtt cgttccactc tgaagtgtc     1260 aagtacatcg caaagtctcc gcaattacac                                      1290
```

<210> SEQ ID NO 41
<211> LENGTH: 351
<212> TYPE: DNA
<213> ORGANISM: Artificial Sequence
<220> FEATURE:
<223> OTHER INFORMATION: ter_rrnB fragment (complement)

<400> SEQUENCE: 41

```
caaaaagagt tgtagaaac gcaaaaggc catccgtcag gatggccttc tgcttaattt      60
gatgcctggc agtttatggc gggcgtcctg cccgccaccc tccggccgt tgcttcgcaa    120
cgttcaaatc cgctcccggc ggatttgtcc tactcaggag agcgttcacc gacaaacaac   180
agataaaacg aaaggcccag tctttcgact gagcctttcg ttttatttga tgcctggcag   240
ttccctactc tcgcatgggg agaccccaca ctaccatcgg cgctacgcg tttcacttct    300
gagttcggca tggggtcagg tgggaccacc gcgctactgc cgccaggcaa a            351
```

<210> SEQ ID NO 42
<211> LENGTH: 2148
<212> TYPE: DNA
<213> ORGANISM: Escherichia coli
<220> FEATURE:
<221> NAME/KEY: CDS
<222> LOCATION: (1)..(2148)

<400> SEQUENCE: 42

```
atg aac gtt att gca ata ttg aat cac atg ggg gtt tat ttt aaa gaa     48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag     96
Glu Pro Ile Arg Glu Leu His Arg Ala Leu Glu Arg Leu Asn Phe Gln
                20                  25                  30 att gtt tac ccg aac gac cgt gac gac tta tta aaa ctg atc gaa aac    144
Ile Val Tyr Pro Asn Asp Arg Asp Asp Leu Leu Lys Leu Ile Glu Asn
            35                  40                  45 aat gcg cgt ctg tgc ggc gtt att ttt gac tgg gat aaa tat aat ctc    192
Asn Ala Arg Leu Cys Gly Val Ile Phe Asp Trp Asp Lys Tyr Asn Leu
        50                  55                  60 gag ctg tgc gaa gaa att agc aaa atg aac gag aac ctg ccg ttg tac    240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg    288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat    336
Arg Leu Gln Ile Ser Phe Phe Glu Tyr Ala Leu Gly Ala Ala Glu Asp
                100                 105                 110 att gct aat aag atc aag cag acc act gac gaa tat atc aac act att    384
Ile Ala Asn Lys Ile Lys Gln Thr Thr Asp Glu Tyr Ile Asn Thr Ile
            115                 120                 125 ctg cct ccg ctg act aaa gca ctg ttt aaa tat gtt cgt gaa ggt aaa    432
Leu Pro Pro Leu Thr Lys Ala Leu Phe Lys Tyr Val Arg Glu Gly Lys
        130                 135                 140 tat act ttc tgt act cct ggt cac atg ggc ggt act gca ttc cag aaa    480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg    528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat    576
Lys Ser Asp Ile Ser Ile Ser Val Ser Glu Leu Gly Ser Leu Leu Asp
                180                 185                 190
```

|  |  |  |  |  |  |  |  |  |  |  |  |  |  |  |  |
|---|---|---|---|---|---|---|---|---|---|---|---|---|---|---|---|
| cac | agt | ggt | cca | cac | aaa | gaa | gca | gaa | cag | tat | atc | gct | cgc | gtc | ttt |
| His | Ser | Gly | Pro | His | Lys | Glu | Ala | Glu | Gln | Tyr | Ile | Ala | Arg | Val | Phe |
|  |  | 195 |  |  |  |  | 200 |  |  |  |  | 205 |  |  |  |

624 aac gca gac cgc agc tac atg gtg acc aac ggt act tcc act gcg aac   672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att   720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg agc gat       768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt   816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc   864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc   912
Val Lys Glu Thr Pro Asn Ala Thr Trp Pro Val His Ala Val Ile Thr
    290                 295                 300 aac tct acc tat gat ggt ctg ctg tac aac acc gac ttc atc aag aaa   960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac  1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc  1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg  1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta  1152
Leu Ala Ala Phe Ser Gln Ala Ser Met Ile His Val Lys Gly Asp Val
    370                 375                 380 aac gaa gaa acc ttt aac gaa gcc tac atg atg cac acc acc act tct  1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg  1248
Pro His Tyr Gly Ile Val Ala Ser Thr Glu Thr Ala Ala Ala Met Met
                405                 410                 415 aaa ggc aat gca ggt aag cgt ctg atc aac ggt tct att gaa cgt gcg  1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc  1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc  1392
Trp Phe Phe Asp Val Trp Gln Pro Asp His Ile Asp Thr Thr Glu Cys
    450                 455                 460 tgg ccg ctg cgt tct gac agc acc tgg cac ggc ttc aaa aac atc gat  1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg  1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc  1536
Gly Met Glu Lys Asp Gly Thr Met Ser Asp Phe Gly Ile Pro Ala Ser

```
                500             505             510
atc gtg gcg aaa tac ctc gac gaa cat ggc atc gtt gtt gag aaa acc      1584
Ile Val Ala Lys Tyr Leu Asp Glu His Gly Ile Val Val Glu Lys Thr
            515             520             525 ggt ccg tat aac ctg ctg ttc ctg ttc agc atc ggt atc gat aag acc      1632
Gly Pro Tyr Asn Leu Leu Phe Leu Phe Ser Ile Gly Ile Asp Lys Thr
530             535             540 aaa gca ctg agc ctg ctg cgt gct ctg act gac ttt aaa cgt gcg ttc      1680
Lys Ala Leu Ser Leu Leu Arg Ala Leu Thr Asp Phe Lys Arg Ala Phe
545             550             555             560 gac ctg aac ctg cgt gtg aaa aac atg ctg ccg tct ctg tat cgt gaa      1728
Asp Leu Asn Leu Arg Val Lys Asn Met Leu Pro Ser Leu Tyr Arg Glu
                565             570             575 gat cct gaa ttc tat gaa aac atg cgt att cag gaa ctg gct cag aat      1776
Asp Pro Glu Phe Tyr Glu Asn Met Arg Ile Gln Glu Leu Ala Gln Asn
            580             585             590 atc cac aaa ctg att gtt cac cac aat ctg ccg gat ctg atg tat cgc      1824
Ile His Lys Leu Ile Val His His Asn Leu Pro Asp Leu Met Tyr Arg
        595             600             605 gca ttt gaa gtg ctg ccg acg atg gta atg act ccg tat gct gca ttc      1872
Ala Phe Glu Val Leu Pro Thr Met Val Met Thr Pro Tyr Ala Ala Phe
610             615             620 cag aaa gag ctg cac ggt atg acc gaa gaa gtt tac ctc gac gaa atg      1920
Gln Lys Glu Leu His Gly Met Thr Glu Glu Val Tyr Leu Asp Glu Met
625             630             635             640 gta ggt cgt att aac gcc aat atg atc ctt ccg tac ccg ccg gga gtt      1968
Val Gly Arg Ile Asn Ala Asn Met Ile Leu Pro Tyr Pro Pro Gly Val
                645             650             655 cct ctg gta atg ccg ggt gaa atg atc acc gaa gaa agc cgt ccg gtt      2016
Pro Leu Val Met Pro Gly Glu Met Ile Thr Glu Glu Ser Arg Pro Val
            660             665             670 ctg gag ttc ctg cag atg ctg tgt gaa atc ggc gct cac tat ccg ggc      2064
Leu Glu Phe Leu Gln Met Leu Cys Glu Ile Gly Ala His Tyr Pro Gly
        675             680             685 ttt gaa acc gat att cac ggt gca tac cgt cag gct gat ggc cgc tat      2112
Phe Glu Thr Asp Ile His Gly Ala Tyr Arg Gln Ala Asp Gly Arg Tyr
690             695             700 acc gtt aag gta ttg aaa gaa gaa agc aaa aaa taa                      2148
Thr Val Lys Val Leu Lys Glu Glu Ser Lys Lys
705             710             715

<210> SEQ ID NO 43
<211> LENGTH: 715
<212> TYPE: PRT
<213> ORGANISM: Escherichia coli

<400> SEQUENCE: 43

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95
```

```
Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510
```

```
Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His Asn Leu Pro Asp Leu Met Tyr Arg
        595                 600                 605

Ala Phe Glu Val Leu Pro Thr Met Val Met Thr Pro Tyr Ala Ala Phe
610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 44
<211> LENGTH: 2142
<212> TYPE: DNA
<213> ORGANISM: Escherichia coli
<220> FEATURE:
<221> NAME/KEY: CDS
<222> LOCATION: (1)..(2142)

<400> SEQUENCE: 44 atg aac atc att gcc att atg gga ccg cat ggc gtc ttt tat aaa gat        48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag        96
Glu Pro Ile Lys Glu Leu Glu Ser Ala Leu Val Ala Gln Gly Phe Gln
                20                  25                  30 att atc tgg cca caa aac agc gtt gat ttg ctg aaa ttt atc gag cat       144
Ile Ile Trp Pro Gln Asn Ser Val Asp Leu Leu Lys Phe Ile Glu His
            35                  40                  45 aac cct cga att tgc ggc gtg att ttt gac tgg gat gag tac agt ctc       192
Asn Pro Arg Ile Cys Gly Val Ile Phe Asp Trp Asp Glu Tyr Ser Leu
        50                  55                  60 gat tta tgt agc gat atc aat cag ctt aat gaa tat ctc ccg ctt tat       240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg       288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat       336
Arg Met Ala Leu Trp Phe Phe Glu Tyr Ala Leu Gly Gln Ala Glu Asp
                100                 105                 110 atc gcc att cgt atg cgt cag tac acc gac gaa tat ctt gat aac att       384
```

```
Ile Ala Ile Arg Met Arg Gln Tyr Thr Asp Glu Tyr Leu Asp Asn Ile
        115                 120                 125 aca ccg ccg ttc acg aaa gcc ttg ttt acc tac gtc aaa gag cgg aag    432
Thr Pro Pro Phe Thr Lys Ala Leu Phe Thr Tyr Val Lys Glu Arg Lys
    130                 135                 140 tac acc ttt tgt acg ccg ggg cat atg ggc ggc acc gca tat caa aaa    480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt    528
Ser Pro Val Gly Cys Leu Phe Tyr Asp Phe Phe Gly Gly Asn Thr Leu
                165                 170                 175 aag gct gat gtc tct att tcg gtc acc gag ctt ggt tcg ttg ctc gac    576
Lys Ala Asp Val Ser Ile Ser Val Thr Glu Leu Gly Ser Leu Leu Asp
            180                 185                 190 cac acc ggg cca cac ctg gaa gcg gaa gag tac atc gcg cgg act ttt    624
His Thr Gly Pro His Leu Glu Ala Glu Glu Tyr Ile Ala Arg Thr Phe
        195                 200                 205 ggc gcg gaa cag agt tat atc gtt acc aac gga aca tcg acg tcg aac    672
Gly Ala Glu Gln Ser Tyr Ile Val Thr Asn Gly Thr Ser Thr Ser Asn
    210                 215                 220 aaa att gtg ggt atg tac gcc gcg cca tcc ggc agt acg ctg ttg atc    720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat    768
Asp Arg Asn Cys His Lys Ser Leu Ala His Leu Leu Met Met Asn Asp
                245                 250                 255 gta gtg cca gtc tgg ctg aaa ccg acg cgt aat gcg ttg ggg att ctt    816
Val Val Pro Val Trp Leu Lys Pro Thr Arg Asn Ala Leu Gly Ile Leu
            260                 265                 270 ggt ggg atc ccg cgc cgt gaa ttt act cgc gac agc atc gaa gag aaa    864
Gly Gly Ile Pro Arg Arg Glu Phe Thr Arg Asp Ser Ile Glu Glu Lys
        275                 280                 285 gtc gct gct acc acg caa gca caa tgg ccg gtt cat gcg gtg atc acc    912
Val Ala Ala Thr Thr Gln Ala Gln Trp Pro Val His Ala Val Ile Thr
    290                 295                 300 aac tcc acc tat gat ggc ttg ctc tac aac acc gac tgg atc aaa cag    960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac   1008
Thr Leu Asp Val Pro Ser Ile His Phe Asp Ser Ala Trp Val Pro Tyr
                325                 330                 335 acc cat ttt cat ccg atc tac cag ggt aaa agt ggt atg agc ggc gag   1056
Thr His Phe His Pro Ile Tyr Gln Gly Lys Ser Gly Met Ser Gly Glu
            340                 345                 350 cgt gtt gcg gga aaa gtg atc ttc gaa acg caa tcg acc cac aaa atg   1104
Arg Val Ala Gly Lys Val Ile Phe Glu Thr Gln Ser Thr His Lys Met
        355                 360                 365 ctg gcg gcg tta tcg cag gct tcg ctg atc cac att aaa ggc gag tat   1152
Leu Ala Ala Leu Ser Gln Ala Ser Leu Ile His Ile Lys Gly Glu Tyr
    370                 375                 380 gac gaa gag gcc ttt aac gaa gcc ttt atg atg cat acc acc acc tcg   1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg   1248
Pro Ser Tyr Pro Ile Val Ala Ser Val Glu Thr Ala Ala Ala Met Leu
                405                 410                 415 cgt ggt aat ccg ggc aaa cgg ctg att aac cgt tca gta gaa cga gct   1296
Arg Gly Asn Pro Gly Lys Arg Leu Ile Asn Arg Ser Val Glu Arg Ala
            420                 425                 430
```

```
ctg cat ttt cgc aaa gag gtc cag cgg ctg cgg gaa gag tct gac ggt    1344
Leu His Phe Arg Lys Glu Val Gln Arg Leu Arg Glu Glu Ser Asp Gly
        435                 440                 445 tgg ttt ttc gat atc tgg caa ccg ccg cag gtg gat gaa gcc gaa tgc    1392
Trp Phe Phe Asp Ile Trp Gln Pro Pro Gln Val Asp Glu Ala Glu Cys
    450                 455                 460 tgg ccc gtt gcg cct ggc gaa cag tgg cac ggc ttt aac gat gcg gat    1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg    1488
Ala Asp His Met Phe Leu Asp Pro Val Lys Val Thr Ile Leu Thr Pro
                485                 490                 495 ggg atg gac gag cag ggc aat atg agc gag gag ggg atc ccg gcg gcg    1536
Gly Met Asp Glu Gln Gly Asn Met Ser Glu Glu Gly Ile Pro Ala Ala
            500                 505                 510 ctg gta gca aaa ttc ctc gac gaa cgt ggg atc gta gta gag aaa acc    1584
Leu Val Ala Lys Phe Leu Asp Glu Arg Gly Ile Val Val Glu Lys Thr
        515                 520                 525 ggc cct tat aac ctg ctg ttt ctc ttt agt att ggc atc gat aaa acc    1632
Gly Pro Tyr Asn Leu Leu Phe Leu Phe Ser Ile Gly Ile Asp Lys Thr
    530                 535                 540 aaa gca atg gga tta ttg cgt ggg ttg acg gaa ttc aaa cgc tct tac    1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa    1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg    1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg    1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg    1872
Ala Phe Asp Thr Leu Pro Glu Met Ile Met Thr Pro His Gln Ala Trp
    610                 615                 620 caa cga caa att aaa ggc gaa gta gaa acc att gcg ctg gaa caa ctg    1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta    1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta    2016
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
    690                 695                 700 cgc gta cga gtc cta aaa atg gcg gga taa                            2142
Arg Val Arg Val Leu Lys Met Ala Gly
705                 710

<210> SEQ ID NO 45
<211> LENGTH: 713
<212> TYPE: PRT
<213> ORGANISM: Escherichia coli

<400> SEQUENCE: 45
```

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
                20                  25                  30

Ile Ile Trp Pro Gln Asn Ser Val Asp Leu Leu Lys Phe Ile Glu His
            35                  40                  45

Asn Pro Arg Ile Cys Gly Val Ile Phe Asp Trp Asp Glu Tyr Ser Leu
        50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
                100                 105                 110

Ile Ala Ile Arg Met Arg Gln Tyr Thr Asp Glu Tyr Leu Asp Asn Ile
                115                 120                 125

Thr Pro Pro Phe Thr Lys Ala Leu Phe Thr Tyr Val Lys Glu Arg Lys
            130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
                180                 185                 190

His Thr Gly Pro His Leu Glu Ala Glu Glu Tyr Ile Ala Arg Thr Phe
            195                 200                 205

Gly Ala Glu Gln Ser Tyr Ile Val Thr Asn Gly Thr Ser Thr Ser Asn
            210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
                260                 265                 270

Gly Gly Ile Pro Arg Arg Glu Phe Thr Arg Asp Ser Ile Glu Glu Lys
            275                 280                 285

Val Ala Ala Thr Thr Gln Ala Gln Trp Pro Val His Ala Val Ile Thr
            290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
                340                 345                 350

Arg Val Ala Gly Lys Val Ile Phe Glu Thr Gln Ser Thr His Lys Met
            355                 360                 365

Leu Ala Ala Leu Ser Gln Ala Ser Leu Ile His Ile Lys Gly Glu Tyr
            370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415
```

```
Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
        435                 440                 445

Trp Phe Asp Ile Trp Gln Pro Gln Val Asp Glu Ala Glu Cys
    450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
            485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
        595                 600                 605

Ala Phe Asp Thr Leu Pro Glu Met Ile Met Thr Pro His Gln Ala Trp
    610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
        675                 680                 685

Phe Glu Thr Asp Ile His Gly Ala Lys Gln Asp Glu Asp Gly Val Tyr
    690                 695                 700

Arg Val Arg Val Leu Lys Met Ala Gly
705                 710

<210> SEQ ID NO 46
<211> LENGTH: 54
<212> TYPE: DNA
<213> ORGANISM: Artificial
<220> FEATURE:
<223> OTHER INFORMATION: cadA-attL

<400> SEQUENCE: 46
tttgctttct tctttcaata ccttaacggt atagcgtgaa gcctgctttt ttat      54

<210> SEQ ID NO 47
<211> LENGTH: 54
<212> TYPE: DNA
<213> ORGANISM: Artificial
<220> FEATURE:
<223> OTHER INFORMATION: cadA-attR

<400> SEQUENCE: 47
```

```
agatatgact atgaacgtta ttgcaatatt gaatcacgct caagttagta taaa          54
```

<210> SEQ ID NO 48
<211> LENGTH: 54
<212> TYPE: DNA
<213> ORGANISM: Artificial
<220> FEATURE:
<223> OTHER INFORMATION: ldcC-attL

<400> SEQUENCE: 48

```
ggaggaacac atgaacatca ttgccattat gggacctgaa gcctgctttt ttat          54
```

<210> SEQ ID NO 49
<211> LENGTH: 53
<212> TYPE: DNA
<213> ORGANISM: Artificial
<220> FEATURE:
<223> OTHER INFORMATION: ldcC-attR

<400> SEQUENCE: 49

```
cgccattttt aggactcgta cgcggtaaac gccgtccgtc aagttagtat aaa           53
```

<210> SEQ ID NO 50
<211> LENGTH: 1434
<212> TYPE: DNA
<213> ORGANISM: Escherichia coli
<220> FEATURE:
<221> NAME/KEY: CDS
<222> LOCATION: (1)..(1434)
<223> OTHER INFORMATION: ptsG

<400> SEQUENCE: 50

| | | | | | | | | | | | | | | | | |
|---|---|---|---|---|---|---|---|---|---|---|---|---|---|---|---|---|
| atg | ttt | aag | aat | gca | ttt | gct | aac | ctg | caa | aag | gtc | ggt | aaa | tcg | ctg | 48 |
| Met | Phe | Lys | Asn | Ala | Phe | Ala | Asn | Leu | Gln | Lys | Val | Gly | Lys | Ser | Leu | |
| 1 | | | | 5 | | | | | 10 | | | | | 15 | | |
| atg | ctg | ccg | gta | tcc | gta | ctg | cct | atc | gca | ggt | att | ctg | ctg | ggc | gtc | 96 |
| Met | Leu | Pro | Val | Ser | Val | Leu | Pro | Ile | Ala | Gly | Ile | Leu | Leu | Gly | Val | |
| | | 20 | | | | | 25 | | | | | 30 | | | | |
| ggt | tcc | gcg | aat | ttc | agc | tgg | ctg | ccc | gcc | gtt | gta | tcg | cat | gtt | atg | 144 |
| Gly | Ser | Ala | Asn | Phe | Ser | Trp | Leu | Pro | Ala | Val | Val | Ser | His | Val | Met | |
| | 35 | | | | | 40 | | | | | 45 | | | | | |
| gca | gaa | gca | ggc | ggt | tcc | gtc | ttt | gca | aac | atg | cca | ctg | att | ttt | gcg | 192 |
| Ala | Glu | Ala | Gly | Gly | Ser | Val | Phe | Ala | Asn | Met | Pro | Leu | Ile | Phe | Ala | |
| 50 | | | | | 55 | | | | | 60 | | | | | | |
| atc | ggt | gtc | gcc | ctc | ggc | ttt | acc | aat | aac | gat | ggc | gta | tcc | gcg | ctg | 240 |
| Ile | Gly | Val | Ala | Leu | Gly | Phe | Thr | Asn | Asn | Asp | Gly | Val | Ser | Ala | Leu | |
| 65 | | | | | 70 | | | | | 75 | | | | | 80 | |
| gcc | gca | gtt | gtt | gcc | tat | ggc | atc | atg | gtt | aaa | acc | atg | gcc | gtg | gtt | 288 |
| Ala | Ala | Val | Val | Ala | Tyr | Gly | Ile | Met | Val | Lys | Thr | Met | Ala | Val | Val | |
| | | | | 85 | | | | | 90 | | | | | 95 | | |
| gcg | cca | ctg | gta | ctg | cat | tta | cct | gct | gaa | gaa | atc | gcc | tct | aaa | cac | 336 |
| Ala | Pro | Leu | Val | Leu | His | Leu | Pro | Ala | Glu | Glu | Ile | Ala | Ser | Lys | His | |
| | | | | 100 | | | | | 105 | | | | | 110 | | |
| ctg | gcg | gat | act | ggc | gta | ctc | gga | ggg | att | atc | tcc | ggt | gcg | atc | gca | 384 |
| Leu | Ala | Asp | Thr | Gly | Val | Leu | Gly | Gly | Ile | Ile | Ser | Gly | Ala | Ile | Ala | |
| | | | 115 | | | | | 120 | | | | | 125 | | | |
| gcg | tac | atg | ttt | aac | cgt | ttc | tac | cgt | att | aag | ctg | cct | gag | tat | ctt | 432 |
| Ala | Tyr | Met | Phe | Asn | Arg | Phe | Tyr | Arg | Ile | Lys | Leu | Pro | Glu | Tyr | Leu | |
| | | 130 | | | | | 135 | | | | | 140 | | | | |
| ggc | ttc | ttt | gcc | ggt | aaa | cgc | ttt | gtg | ccg | atc | att | tct | ggc | ctg | gct | 480 |
| Gly | Phe | Phe | Ala | Gly | Lys | Arg | Phe | Val | Pro | Ile | Ile | Ser | Gly | Leu | Ala | |
| 145 | | | | | 150 | | | | | 155 | | | | | 160 | |
| gcc | atc | ttt | act | ggc | gtt | gtg | ctg | tcc | ttc | att | tgg | ccg | ccg | att | ggt | 528 |

```
Ala Ile Phe Thr Gly Val Val Leu Ser Phe Ile Trp Pro Pro Ile Gly
            165                 170                 175 tct gca atc cag acc ttc tct cag tgg gct gct tac cag aac ccg gta      576
Ser Ala Ile Gln Thr Phe Ser Gln Trp Ala Ala Tyr Gln Asn Pro Val
            180                 185                 190 gtt gcg ttt ggc att tac ggt ttc atc gaa cgt tgc ctg gta ccg ttt      624
Val Ala Phe Gly Ile Tyr Gly Phe Ile Glu Arg Cys Leu Val Pro Phe
            195                 200                 205 ggt ctg cac cac atc tgg aac gta cct ttc cag atg cag att ggt gaa      672
Gly Leu His His Ile Trp Asn Val Pro Phe Gln Met Gln Ile Gly Glu
            210                 215                 220 tac acc aac gca gca ggt cag gtt ttc cac ggc gac att ccg cgt tat      720
Tyr Thr Asn Ala Ala Gly Gln Val Phe His Gly Asp Ile Pro Arg Tyr
225                 230                 235                 240 atg gcg ggt gac ccg act gcg ggt aaa ctg tct ggt ggc ttc ctg ttc      768
Met Ala Gly Asp Pro Thr Ala Gly Lys Leu Ser Gly Gly Phe Leu Phe
                245                 250                 255 aaa atg tac ggt ctg cca gct gcc gca att gct atc tgg cac tct gct      816
Lys Met Tyr Gly Leu Pro Ala Ala Ala Ile Ala Ile Trp His Ser Ala
                260                 265                 270 aaa cca gaa aac cgc gcg aaa gtg ggc ggt att atg atc tcc gcg gcg      864
Lys Pro Glu Asn Arg Ala Lys Val Gly Gly Ile Met Ile Ser Ala Ala
                275                 280                 285 ctg acc tcg ttc ctg acc ggt atc acc gag ccg atc gag ttc tcc ttc      912
Leu Thr Ser Phe Leu Thr Gly Ile Thr Glu Pro Ile Glu Phe Ser Phe
            290                 295                 300 atg ttc gtt gcg ccg atc ctg tac atc atc cac gcg att ctg gca ggc      960
Met Phe Val Ala Pro Ile Leu Tyr Ile Ile His Ala Ile Leu Ala Gly
305                 310                 315                 320 ctg gca ttc cca atc tgt att ctt ctg ggg atg cgt gac ggt acg tcg     1008
Leu Ala Phe Pro Ile Cys Ile Leu Leu Gly Met Arg Asp Gly Thr Ser
                325                 330                 335 ttc tcg cac ggt ctg atc gac ttc atc gtt ctg tct ggt aac agc agc     1056
Phe Ser His Gly Leu Ile Asp Phe Ile Val Leu Ser Gly Asn Ser Ser
                340                 345                 350 aaa ctg tgg ctg ttc ccg atc gtc ggt atc ggt tat gcg att gtt tac     1104
Lys Leu Trp Leu Phe Pro Ile Val Gly Ile Gly Tyr Ala Ile Val Tyr
            355                 360                 365 tac acc atc ttc cgc gtg ctg att aaa gca ctg gat ctg aaa acg ccg     1152
Tyr Thr Ile Phe Arg Val Leu Ile Lys Ala Leu Asp Leu Lys Thr Pro
            370                 375                 380 ggt cgt gaa gac gcg act gaa gat gca aaa gcg aca ggt acc agc gaa     1200
Gly Arg Glu Asp Ala Thr Glu Asp Ala Lys Ala Thr Gly Thr Ser Glu
385                 390                 395                 400 atg gca ccg gct ctg gtt gct gca ttt ggt ggt aaa gaa aac att act     1248
Met Ala Pro Ala Leu Val Ala Ala Phe Gly Gly Lys Glu Asn Ile Thr
                405                 410                 415 aac ctc gac gca tgt att acc cgt ctg cgc gtc agc gtt gct gat gtg     1296
Asn Leu Asp Ala Cys Ile Thr Arg Leu Arg Val Ser Val Ala Asp Val
            420                 425                 430 tct aaa gtg gat cag gcc ggc ctg aag aaa ctg ggc gcg gcg ggc gta     1344
Ser Lys Val Asp Gln Ala Gly Leu Lys Lys Leu Gly Ala Ala Gly Val
            435                 440                 445 gtg gtt gct ggt tct ggt gtt cag gcg att ttc ggt act aaa tcc gat     1392
Val Val Ala Gly Ser Gly Val Gln Ala Ile Phe Gly Thr Lys Ser Asp
450                 455                 460 aac ctg aaa acc gag atg gat gag tac atc cgt aac cac taa              1434
Asn Leu Lys Thr Glu Met Asp Glu Tyr Ile Arg Asn His
465                 470                 475
```

<210> SEQ ID NO 51
<211> LENGTH: 477
<212> TYPE: PRT
<213> ORGANISM: Escherichia coli

<400> SEQUENCE: 51

```
Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
                20                  25                  30

Gly Ser Ala Asn Phe Ser Trp Leu Pro Ala Val Val Ser His Val Met
            35                  40                  45

Ala Glu Ala Gly Gly Ser Val Phe Ala Asn Met Pro Leu Ile Phe Ala
        50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
            100                 105                 110

Leu Ala Asp Thr Gly Val Leu Gly Gly Ile Ile Ser Gly Ala Ile Ala
        115                 120                 125

Ala Tyr Met Phe Asn Arg Phe Tyr Arg Ile Lys Leu Pro Glu Tyr Leu
    130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
        275                 280                 285

Leu Thr Ser Phe Leu Thr Gly Ile Thr Glu Pro Ile Glu Phe Ser Phe
    290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
            340                 345                 350

Lys Leu Trp Leu Phe Pro Ile Val Gly Ile Gly Tyr Ala Ile Val Tyr
        355                 360                 365

Tyr Thr Ile Phe Arg Val Leu Ile Lys Ala Leu Asp Leu Lys Thr Pro
    370                 375                 380
```

-continued

```
Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415

Asn Leu Asp Ala Cys Ile Thr Arg Leu Arg Val Ser Val Ala Asp Val
                420                 425                 430

Ser Lys Val Asp Gln Ala Gly Leu Lys Lys Leu Gly Ala Ala Gly Val
                435                 440                 445

Val Val Ala Gly Ser Gly Val Gln Ala Ile Phe Gly Thr Lys Ser Asp
        450                 455                 460

Asn Leu Lys Thr Glu Met Asp Glu Tyr Ile Arg Asn His
465                 470                 475
```